(12) United States Patent
Serda et al.

(10) Patent No.: US 8,926,994 B2
(45) Date of Patent: Jan. 6, 2015

(54) MESOPOROUS SILICON PARTICLES FOR THE PRESENTATION OF TUMOR ANTIGENS AND ADJUVANT FOR ANTI-CANCER IMMUNITY

(71) Applicant: The Methodist Hospital Research Institute, Houston, TX (US)

(72) Inventors: Rita Elena Serda, Pearland, TX (US); Ismail Mustafa Meraz, Pearland, TX (US); Jianhua Gu, Houston, TX (US); Xiaojun Xia, Houston, TX (US); Haifa Shen, Bellaire, TX (US); Tong Sun, Houston, TX (US); Mauro Ferrari, Houston, TX (US)

(73) Assignee: The Methodist Hospital Research Institute, Houston, TX (US)

( * ) Notice: Subject to any disclaimer, the term of this patent is extended or adjusted under 35 U.S.C. 154(b) by 0 days.

(21) Appl. No.: 13/708,888

(22) Filed: Dec. 7, 2012

(65) Prior Publication Data

US 2013/0195963 A1    Aug. 1, 2013

Related U.S. Application Data

(60) Provisional application No. 61/568,055, filed on Dec. 7, 2011.

(51) Int. Cl.
*A61K 39/00* (2006.01)
*A61K 47/48* (2006.01)
*A61K 9/14* (2006.01)

(52) U.S. Cl.
CPC ....... *A61K 9/143* (2013.01); *A61K 2039/55572* (2013.01); *A61K 47/48861* (2013.01); *A61K 2039/55555* (2013.01); *A61K 2039/55561* (2013.01); *A61K 47/48876* (2013.01); *A61K 39/0011* (2013.01)
USPC .......... 424/277.1; 424/489; 424/490

(58) Field of Classification Search
None
See application file for complete search history.

(56) References Cited

U.S. PATENT DOCUMENTS

2005/0112199 A1* 5/2005 Padval et al. ................. 424/468
2008/0311182 A1* 12/2008 Ferrari et al. ................. 424/450

OTHER PUBLICATIONS

UC Nygaard, JS Hansen, M Samuelsen, T Alberg, CD Marioara, M Lovik. "Single-Walled and Multi-Walled Carbon Nanotubes Promote Allergic Immune Responses in Mice." Toxicological Sciences, vol. 109(1), 2009, pp. 113-123.*

* cited by examiner

*Primary Examiner* — Frederick Krass
*Assistant Examiner* — Isaac Shomer
(74) *Attorney, Agent, or Firm* — Haynes and Boone, LLP

(57) ABSTRACT

Disclosed are mesoporous silicon multi-stage vehicles that comprise liposomal-based second-stage particles, as well as pharmaceutical compositions and formulations including such vectors for use in a variety of diagnostic and therapeutic indications. In particular embodiments, MSV comprising ligand decorated second-stage particles are provided for therapeutic methods including, for example, treatment of mammalian cancers, including those of the human breast.

36 Claims, 16 Drawing Sheets

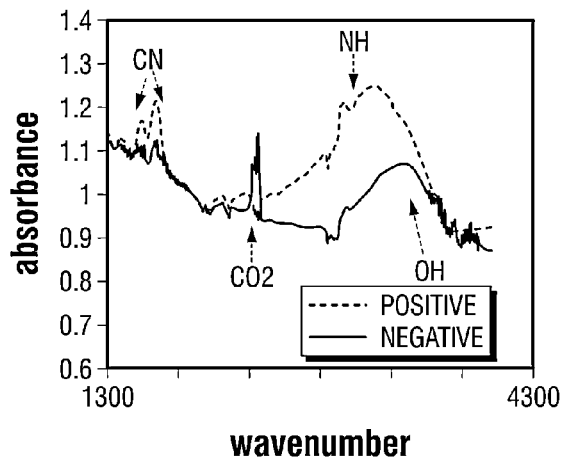
FIG. 13A
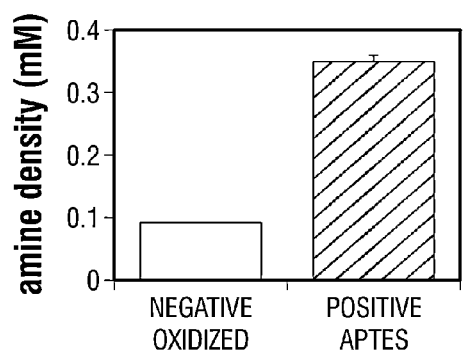
FIG. 13B
| ZETA POTENTIAL (MV) | | | | |
|---|---|---|---|---|
| | CONTROL | SERUM | | |
| | | 4°C | 25°C | 37°C |
| CATIONIC | 27.9 | 3.8 | 3.0 | 5.5 |
| ANIONIC | -19.4 | 1.8 | 1.2 | 2.0 |
FIG. 13C
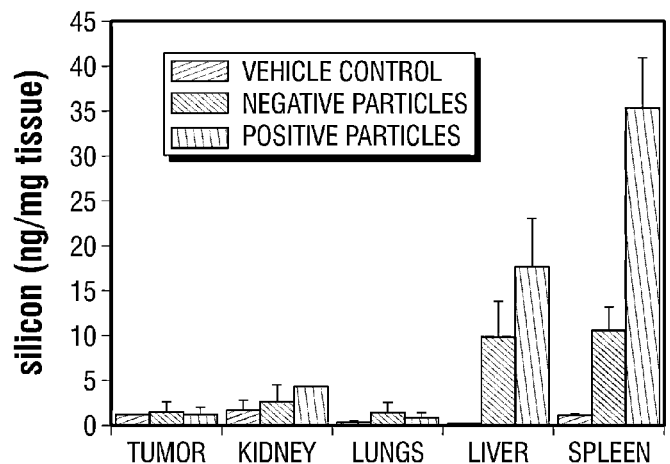
FIG. 14A

MESOPOROUS SILICON PARTICLES FOR THE PRESENTATION OF TUMOR ANTIGENS AND ADJUVANT FOR ANTI-CANCER IMMUNITY

CROSS-REFERENCE TO RELATED APPLICATIONS

The application claims the benefit of the filing date of U.S. patent application No. 61/568,055, filed on Dec. 7, 2011, the disclosure of which is incorporated herein by reference.

STATEMENT REGARDING FEDERALLY SPONSORED RESEARCH OR DEVELOPMENT

This invention was made with government support under Grant Nos. W81XWH-09-1-0212 from the United States Department of Defense. The government has certain rights in the invention.

NAMES OF THE PARTIES TO A JOINT RESEARCH AGREEMENT

Not Applicable.

BACKGROUND OF THE INVENTION

1. Field of the Invention

The present invention relates to the fields of molecular biology and medicine. Mesoporous silicon particles and compositions comprising them are provided for use in a variety of diagnostic and therapeutic indications. In particular, nanoparticle-loaded pSi particles for the presentation of tumor antigens and as adjuvants for anti-cancer immunity have been developed.

2. Description of Related Art

Adjuvants

Aluminum-based adjuvants, designed to enhance immune responses to antigens, were introduced in the 1920s, and 91 years later, they remain the standard adjuvant used in vaccines. Studies on new nanoparticle-based vaccines are increasing, with the advantage of combining adjuvant and antigen in a single entity. These particles are rapidly internalized by antigen-presenting cells (APC) with trafficking to lymphoid tissue for presentation to lymphocytes.

Nanotechnology

Nanotechnology pertains to synthetic, engineerable objects that are nanoscale in dimensions or have critical functioning nanoscale components, leading to novel, unique properties (Ferrari, 2005; Theis et al., 2006). These emergent characteristics arise from the material's large surface area and nanoscopic size (Riehemann, 2009). Nanotechnology now occupies a niche as a burgeoning and revolutionary field within medicine known as nanomedicine, particularly within the field of oncology (Ferrari, 2005). One of the potential benefits of nanomedicine is the creation of nanoparticle-based vectors that deliver therapeutic cargo in sufficient quantity to a target lesion to enable a selective effect. This is a daunting task for all drug molecules, owing to the highly organized array of 'biological barriers' that the molecules encounter (Riehemann, 2009; Jain, 1989; Jain, 1999; Sakamoto et al., 2007). The human body presents a robust defense system that is extremely effective in preventing injected chemicals, biomolecules, nanoparticles and any other foreign agents from reaching their intended destinations. Biobarriers are sequential in nature, and therefore, the probability of reaching the therapeutic objective is the product of individual probabilities of overcoming each barrier (Ferrari, 2005; Ferrari, 2009). Sequentially (with respect to intravascular injections) these comprise: 1) enzymatic degradation; 2) sequestration by phagocytes of the reticulo-endothelial system (RES) (Caliceti and Veronese, 2003; Moghimi and Davis, 1994); 3) vascular endothelia (Mehta and Malik, 2006); 4) adverse oncotic and interstitial pressures in the tumor (Stohrer et al., 2000; Less et al., 1992); 5) cellular membranes, or subcellular organelles such as the nucleus and endosomes (Torchilin, 2006; Majumdar and Mitra, 2006); and 6) molecular efflux pumps (Undevia et al., 2005). Without an effective strategy to negotiate these barriers, new or current therapeutic agents based on enhanced biomolecular selectivity may yield sub-optimal utility, simply because they reach the intended targets in very small fractions, with only 1 in 10,000 to 1 in 100,000 molecules reaching their intended site of action (Ferrari, 2005). Due to this narrow therapeutic window, marginal tolerability and considerable mortality ensue (Canal et al., 1998). Transport through different compartments and across biological barriers can be enhanced by optimization of particle size, shape, density and surface chemistry. These parameters dominate transport in the bloodstream, margination, cell adhesion, selective cellular uptake, and sub-cellular trafficking.

An early obstacle for intravascularly administered therapeutics is the endothelial wall that forms the boundary between the circulatory system and tissue specific microenvironments. Specific adherence of delivery vectors to diseased vasculature provides a key to conquering this early barrier, as does the hijacking of cells bound for the inflammatory microenvironment of the lesion. In particular, what is lacking in the prior art are compositions and methods for efficiently overcoming various bio-barriers that employ multiple levels of targeting, spatial release of secondary carriers or therapeutics, simultaneous delivery of independent systems and/or systems capable of synergistic impact.

BRIEF SUMMARY OF THE INVENTION

The present invention overcomes these and other inherent limitations in the art by providing, in a general sense, mesoporous silicon particles for use in a variety of diagnostic and therapeutic indications. In illustrative embodiments, nanoparticle-loaded pSi particles for the presentation of tumor antigens and as adjuvants for anti-cancer immunity have been developed.

In one embodiment, the present invention provides cancer vaccines that utilize an array of tumor antigens conjugated to the surface of nanoparticles (i.e., tumor mimetics). The tumor mimetics are co-loaded into a larger carrier particle in association with an expression vector, creating both a vehicle for tumor antigens and a source for cytokine production (i.e., multifunctional vector vaccines). The ultimate outcome is presentation of tumor antigens in association with major histocompatibility complex and co-stimulatory molecules by APC for the induction of tumor-specific immunogenicity.

In a first embodiment, the invention provides, in an overall and general sense, a composition that includes at least one first-stage porous or nanoporous silicon oxide micro or nanoparticle and which has (i) a body, (ii) at least one surface; and (iii) at least one reservoir inside the body, such that the reservoir contains at least one second-stage particle that comprises at least a first active agent. Preferably, the body of the first-stage particle comprises a biocompatible or biodegradable material such as a nanoporous silicon dioxide, a nanoporous aluminum oxide, a nanoporous titanium oxide, a nanoporous iron oxide or one or more combinations thereof. In certain embodiments, the body of the first-stage particle comprises a first porous region and a second porous region that differs from the first porous region in at least one property selected from the group of properties consisting of pore density, pore geometry, pore charge, pore surface chemistry and pore orientation.

In certain aspects, the first porous region is adapted and configured to contain at least a first population of second-stage particles, and the second porous region is also adapted and configured to contain at least a second population of second-stage particles. The body of the first stage particle preferably includes at least a first region that contains a first population of second-stage particles and a second region containing a second population of second-stage particles.

In illustrative embodiments, the first population of second-stage particles includes one or more liposomes, nanoliposomes, or a combination thereof.

In certain embodiments, the first population of second-stage particles will preferably further include at least a first diagnostic therapeutic or chemotherapeutic agent, and may preferably further include one or more adjuvants, ligands, targeting moieties, or any combination thereof.

In certain embodiment, the invention provides multistage vectors (MSV) in which one or more of the first- and/or second-stage particle include at least one or more tissue-, cellular-, or subcellular-targeting moieties, either alone, and or in combination with one or more additional compounds such as, without limitation, an adjuvant, a protein, a peptide, a ligand, a ligand receptor, an antibody, a linker, a surface receptor, or one or more additional vaccine components, including, without limitation, one or more therapeutic compounds and/or diagnostic or imaging reagents.

Exemplary targeting moieties include, without limitation, a chemical targeting moiety, a physical targeting moiety, a ligand moiety, a ligand targeting moiety, a geometrical targeting moiety, and any combination thereof. In certain embodiments, the at least one targeting moiety is selected from the group consisting of a size of the body of the first stage particle; a shape of the body of the first stage particle; a charge on the surface of the first stage particle; a chemical modification of the first stage particle, and any combination thereof. In practical aspects, the at least one targeting moiety preferably includes one or more chemical targeting moieties disposed on or about at least a first surface of the first-stage and/or the second-stage particle. Preferably, the chemical targeting moiety includes at least one moiety selected from a the group consisting of a ligand, a dendrimer, an oligomer, an aptamer, a binding protein, an antibody, an antigen binding fragment thereof, a biomolecule, an siRNA, and any combination thereof.

In certain aspects, the first- and/or second-stage particles will further contain at least one additional agent, including, without limitation, at least one penetration enhancer, at least one therapeutic and/or chemotherapeutic agent, at least one targeting moiety, and/or at least one or more surface-exposed, surface-bound, surface expressed, or surface contained targeting moieties, either alone, or in combination with one or more adjuvanting or immunomodulatory components and such like.

In some embodiments, the first stage particle is adapted and configured to release the at least one second stage particle in response to an external stimulus or to a change in the environment of the first stage particle.

The preferred second-stage particles of the invention preferably include one or more constituents selected from the group consisting of a liposome, a micelle, an ethosome, a nanosome, a nanoliposomes, a carbon nanotube, a fullerene nanoparticle, a metal nanoparticle, a semiconductor nanoparticle, a polymer nanoparticle, an oxide nanoparticle, a viral particle, a polyionic particle, a ceramic particle, and combinations thereof.

In particular diagnostic and/or therapeutic regimens, the second-stage particles of the present invention will preferably include at least one targeting moiety, and optionally, one or more third-stage particles that include a first active ingredient, therapeutic agent, and/or diagnostic reagent, or any combination thereof.

In certain aspects, the second-stage particle will include one or more portions or bodies that include, or substantially contain on or more selected agents and/or targeting and/or adjuvanting components as discussed herein.

In illustrative embodiments, the second-stage particles include a body and a reservoir inside the body, such that the reservoir of the second-stage particle is substantially adapted to contain substantially all of the active ingredients and/or agents to be delivered to the selected subject of interest.

As described herein, the active agent preferably includes one or more prophylactic agents, one or more therapeutic agents, one or more diagnostic agents, one or more vaccines, one or more imaging agents, one or more radiolabels, one or more adjuvanting agents, one or more chemotherapeutic agents, one or more cytotoxic agents, or any combination thereof.

In related embodiments, the invention also provides therapeutic and/or diagnostic kits including one or more of the compositions disclosed herein, typically in combination with one or more pharmaceutically acceptable carriers, one or more devices for administration of the compositions to a subject of interest, as well as one or more instruction sets for using the composition in the prevention, the diagnosis, or the treatment of a mammalian condition, disease, disorder, trauma, and/or dysfunction, including, without limitation, one or more cancers such as human breast cancer and such like.

The invention also provides in an overall and general sense, methods for providing an active agent to a mammalian dendritic cell comprising administering to the subject, an effective amount of one or more of the MSV compositions disclosed herein. In certain embodiments, the subject is at risk for, diagnosed with, or suspected of having one or more abnormal conditions, including, for example, one or more cancers or other hyperproliferative disorders.

As noted herein, the compositions of the present invention may further optionally include one or more additional therapeutic agents, diagnostic agents, imaging agents, or a combination thereof.

The invention provides a method for administering an active agent to one or more cells, tissues, organs, or systems of a mammalian subject in need thereof. The method generally involves providing to a mammalian subject in need thereof, one or more of the compositions disclosed herein in an amount and for a time effective to administer the active agents contained with the MSV particles to one or more selected tissues, organs, systems, or cells within or about the body of the subject. In particularly preferred embodiments, the subject is a human, and the composition comprises a first stage particle that is adapted and configured to localize to at a first target site within or about the body of the human patient to which the active agent is being administered.

In certain methods, the MSV vaccine components a first-stage particle that is adapted and configured to bypass or "cross" a biological barrier selected from the group consisting of a hemo-rheology barrier, a reticuloendothelial system barrier, an endothelial barrier, a blood brain barrier, a tumor-associated osmotic interstitial pressure barrier, an ionic and molecular pump barrier, a cell membrane barrier, an enzymatic degradation barrier, a nuclear membrane barrier, and any combination thereof.

In particular embodiments, the MSV compositions of the present invention may be formulated for pharmaceutical administration, such as in a suspension that includes a plurality of first-stage particles, and contained substantially there within, a plurality of second-stage particles that include one or more populations of third-stage particles, adjuvants, active ingredients, or any combination thereof.

The compositions of the invention may include a population of first-stage particles that is adapted and configured to separate into a first component comprising the first region and a second component comprising the second region when administered to the subject. In such applications, the body of the first stage particle may include one or more active ingredients, and the second stage particle may contain one or more additional, and distinct, active ingredients.

As noted herein, the compositions of the present invention may be administered to the subject through any one or more conventional methods for administration, including, without limitation, orally, intranasally, intravenously, subcutaneously, or by direct injection to one or more cells or one or more tissues within or about the body of the subject.

As further described herein, in certain applications, it may be desirable to contact a population of cells obtained from a subject ex vivo with the MSV composition, and then, subsequently, to reintroduce the resulting contacted cells into the body of the subject. Such ex vivo therapy is particularly contemplated to be useful in introducing the disclosed particles to populations of human dendritic cells, allowing the active ingredients to be contacted with the cells, and then to re-introduce the resulting cells back into the body of the animal. Preferably, the cells extracted for such ex vivo manipulation will be those of the actual patient undergoing treatment.

BRIEF DESCRIPTION OF THE DRAWINGS

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The invention may be better understood by reference to the following description taken in conjunction with the accompanying drawings, in which like reference numerals identify like elements, and in which:

In FIG. 3D, mice were injected with the particle-based vaccine prior to inoculation with the tumor cells. While a single injection of the particles (red bars) reduced tumor growth with time, repeated injections at escalating doses (3X) lead to a further decrease in tumor growth (green bars, control in blue). Representative mice at the end of the study are shown for each group with the tumor luminescence show in blue, indicating tumor size. The same numbers of tumor cells were injected in each mouse and graphs are based on tumor measurements made with calipers. The data supports both preventative and therapeutic benefits of using TLR-L porous silicon particles for therapy;

Figure 10A:
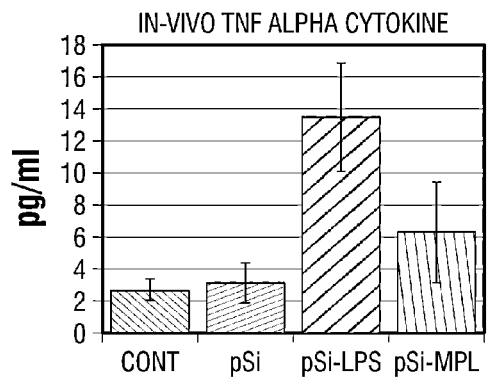
FIG. 10A, FIG. 10B, FIG. 10C, FIG. 10D, FIG. 10E, and FIG. 10F show the in vivo and in vitro pro-inflammatory cytokine production in BMDC by LPS and MPL conjugated porous silicon particles. Inoculation of mice with pSi-LPS bound silicon particles caused more TNF-alpha (FIG. 10A), IL-6 (FIG. 10B) and IL-1 beta (FIG. 10C) production than inoculation with control particles. Innoculation with MPL-bound particles also increased cytokine production, but at lower levels.
Figure 10B:
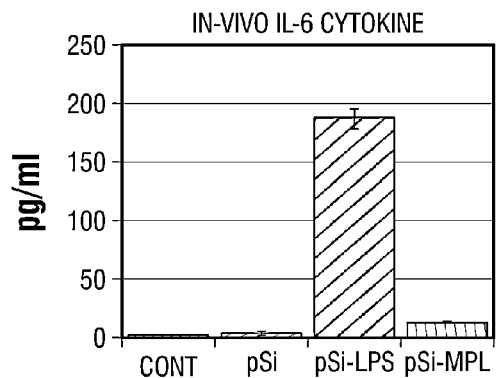
Figure 10C:
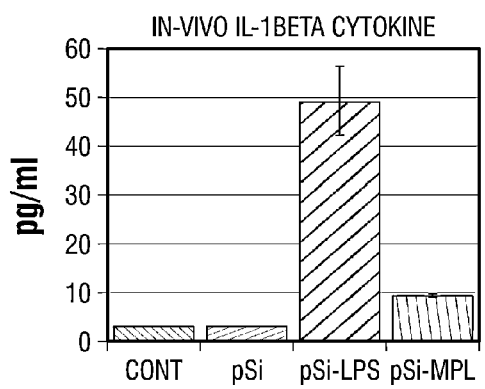
Figure 10D:
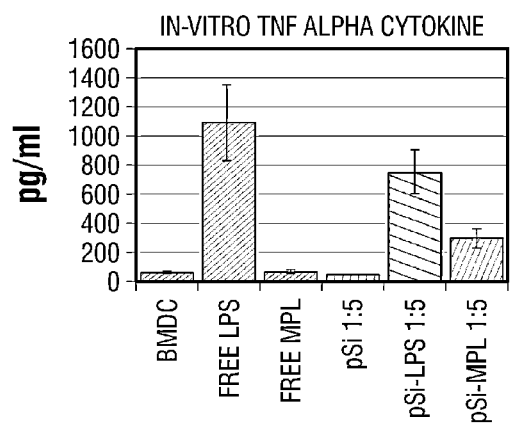
Figure 10E:
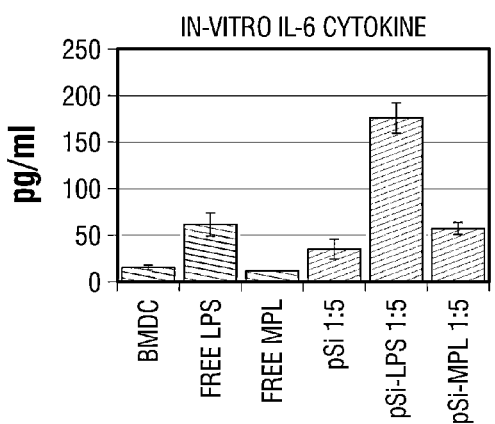
Figure 10F:
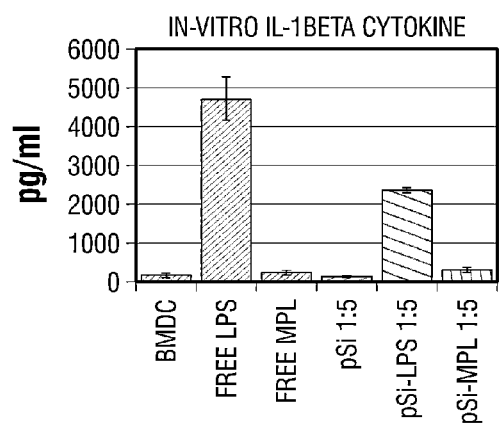
Figure 11A:
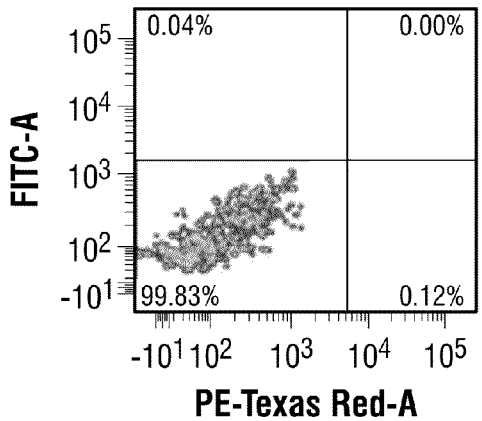
Figure 11B:
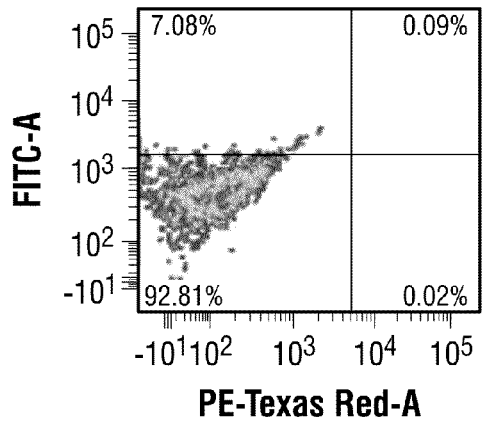
Figure 11C:
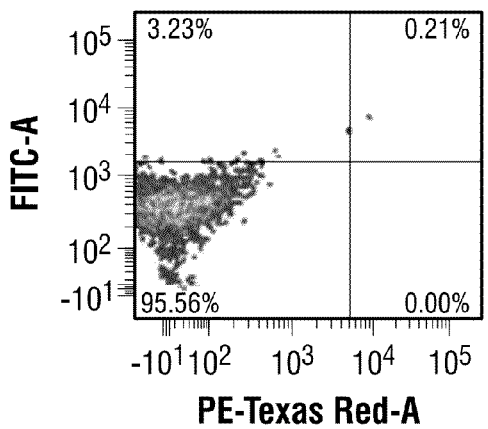
Figure 11D:
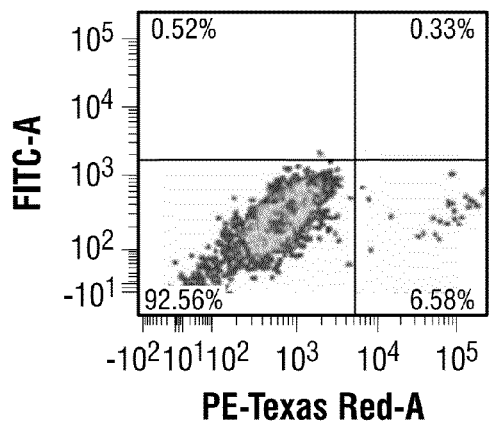
Figure 11E:
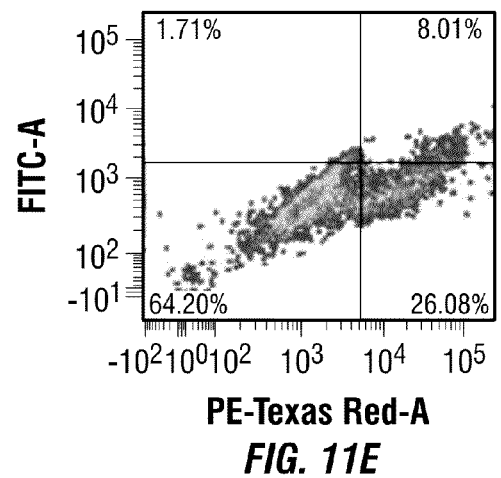
Figure 12A:
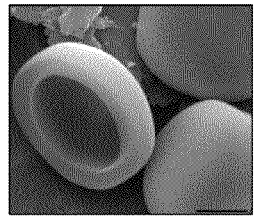
Figure 12B:
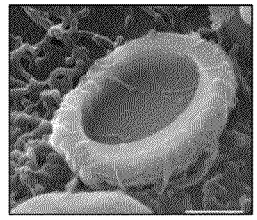
Figure 12C:
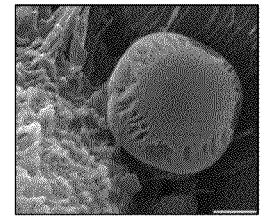
Figure 12D:
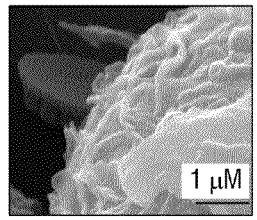
Figure 12E:
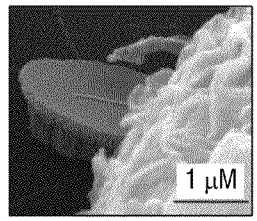
Figure 12F:
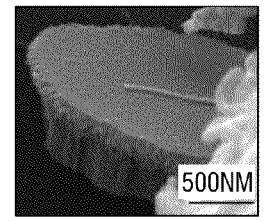
Figure 12G:
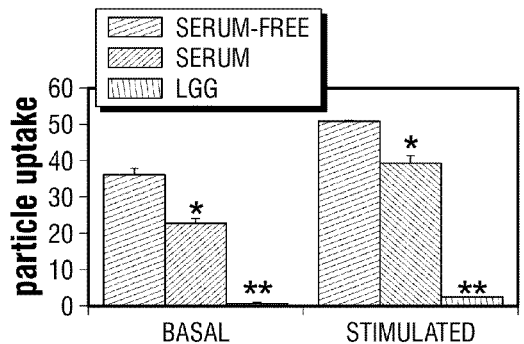
Figure 12H:
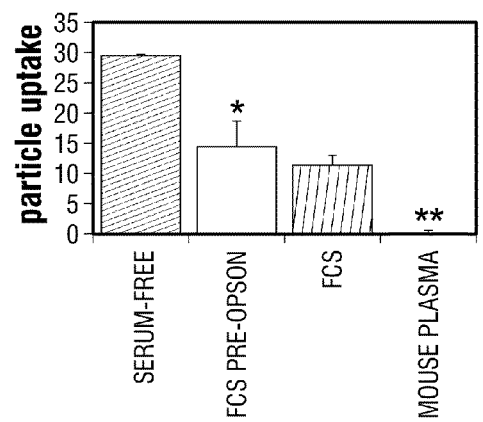
Figure 14B:
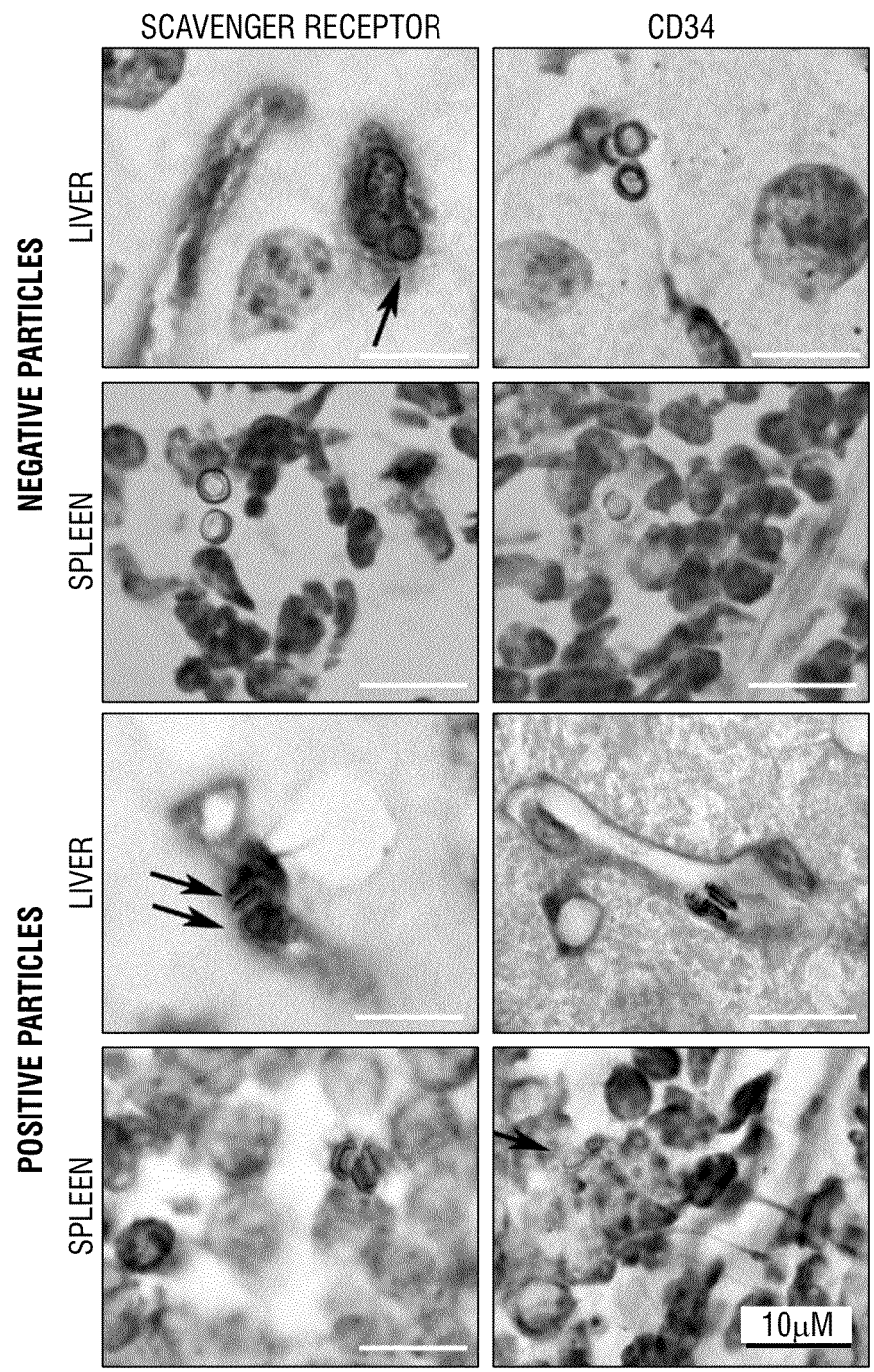
Figure 15A:
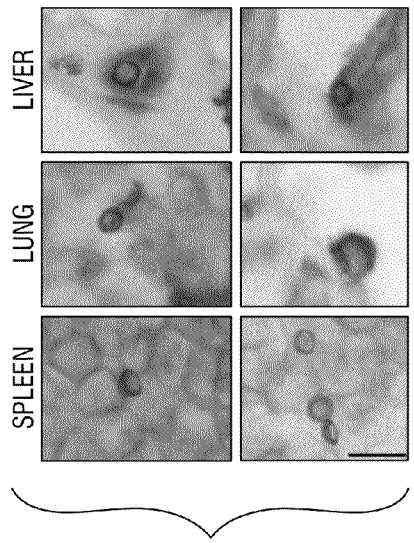
Figure 15B:
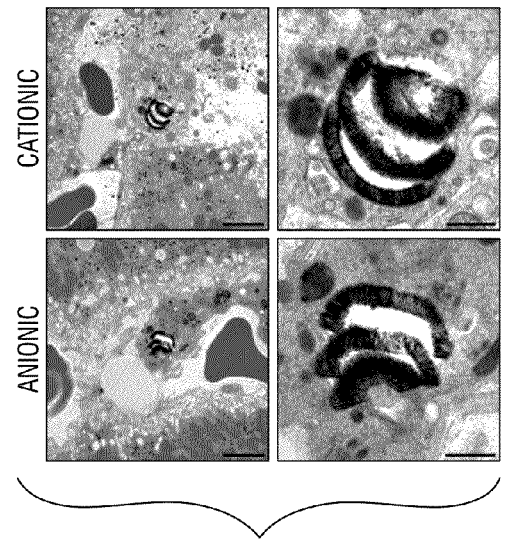
Figure 16A:
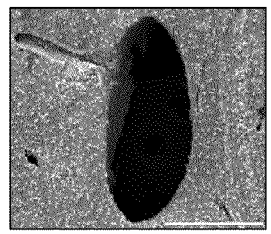
Figure 16B:
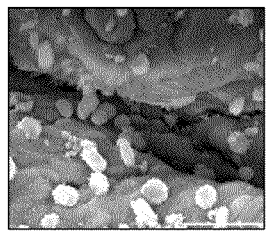
Figure 16C:
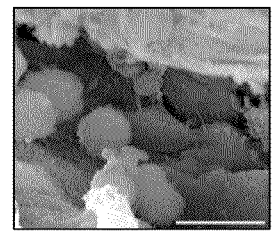
Figure 16D:
Figure 16E:
Figure 16F:
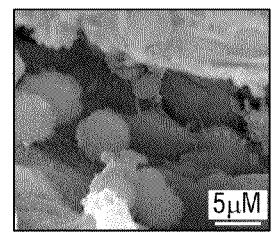
Figure 17A:
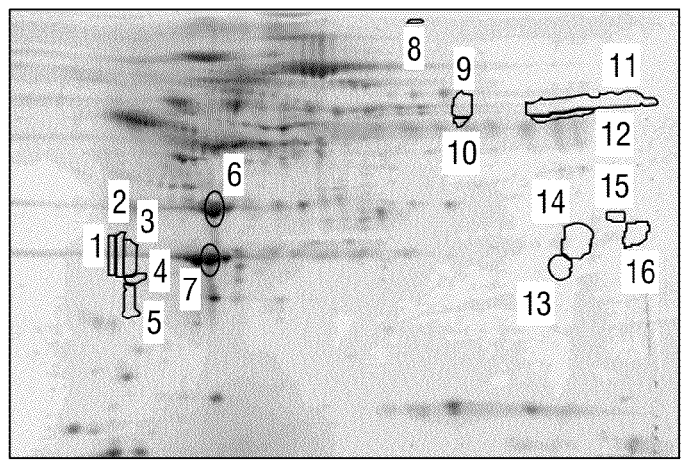
Figure 17B:
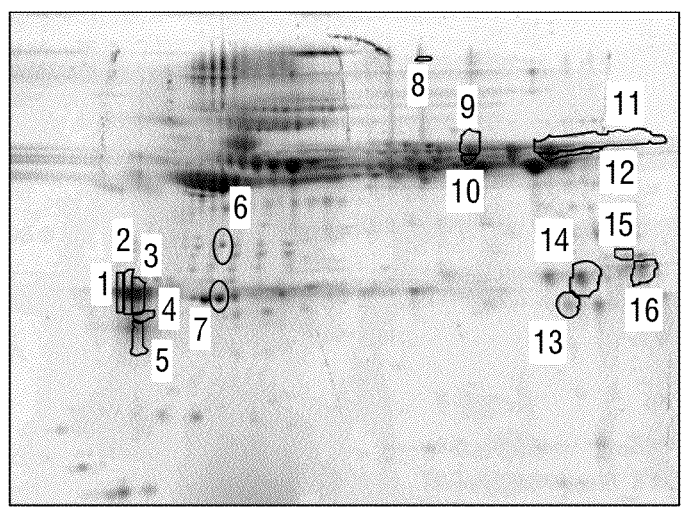
Figure 18A:
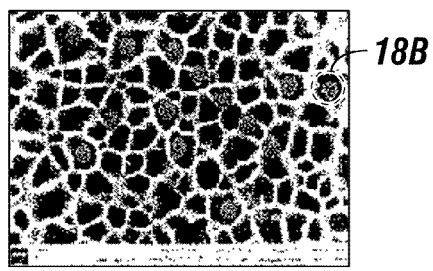
Figure 18B:
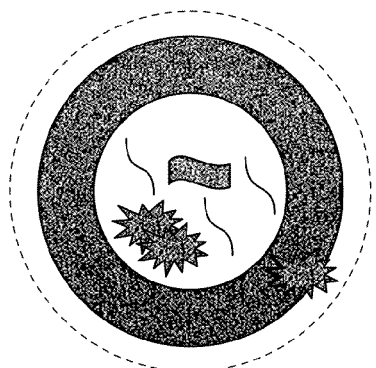

In vitro incubation of BMDC with pSi-LPS also stimulated greater TNF-alpha (FIG. 10D), IL-6 (FIG. 10E) and IL-1 beta (FIG. 10F) secretion than control particles, with MPL-bound silicon particles again inducing weaker production of cytokines than LPS bound particles. Increased levels of IL-1β indicate activation of the inflammasome in antigen presenting cells induced by our TLR-L bound microparticles;

FIG. 11A, FIG. 11B, FIG. 11C, FIG. 11D, and FIG. 11E shows migration of ex-vivo matured DC to the lymph node following injection of the cells labeled with a red fluorescent molecule. Mice were injected with nothing (FIG. 11A), unlabeled DC (FIG. 11B), with LPS (FIG. 11C), with red DC (FIG. 11D), or with red DC following exposure to LPS-bound microparticles (FIG. 11E). Particle-loaded DC showed much greater migration to the lymph node than control DC based on flow cytometry analysis of cells isolated from extracted lymph nodes. The green FITC label is a measure of the LPS that is bound to the particles contained within the red DC);

FIG. 12A, FIG. 12B, FIG. 12C, FIG. 12D, FIG. 12E, FIG. 12F, FIG. 12G, and FIG. 12H show the in vitro cellular associations with porous silicon microparticles. FIG. 12A, FIG. 12B, and FIG. 12C: Two shapes of porous silicon microparticles, quasi-hemispherical (FIG. 12A and FIG. 12B) and discoidal (FIG. 12C), are shown in scanning electron micrographs (bars 1 μm). FIG. 12D, FIG. 12E, and FIG. 12F show scanning electron micrographs of a cell internalizing a discoidal silicon microparticle at increasing magnification. FIG. 12G shows impact of serum protein binding and pro-inflammatory cytokines (stimulated) on endothelial association with anionic silicon microparticles (adapted from Serda et al.,[15]). FIG. 12H shows endothelial association with anionic silicon microparticles in media containing plasma or FCS (fetal calf serum), with and without pre-opsonization of microparticles;

FIG. 13A, FIG. 13B, and FIG. 13C show the characterization of silicon microparticles. FIG. 13A: FTIR analysis of positive (APTES) and negative (oxidized) silicon microparticles. FIG. 13B: Amine density on discoidal microparticles, before and after APTES modification. FIG. 13C: Zeta potential analysis of silicon microparticles before (control) and after incubation in serum at different temperatures for 30 min;

FIG. 14A and FIG. 14B show the tissue biodistribution and cellular associations with silicon microparticles. FIG. 14A: ICP-AES analysis of silicon content in tissues following intravenous injection of saline or microparticles, either positive or negative. FIG. 14B: Histological evaluation of in vivo microparticle association with macrophages and endothelial in liver and spleen based on surface charge (bars 10 μm);

FIG. 15A and FIG. 15B show the tissue specific uptake of silicon microparticles by macrophages. FIG. 15A: Histological evaluation of in vivo microparticle association with macrophages from liver, lung, and spleen (100× oil immersion lens; bars 10 μm). FIG. 15B: Tissue TEM images showing silicon microparticles internalized by hepatic macrophages (Kupffer cells). Each tissue is presented at 10 and 60 k magnification [bars 10 μm (FIG. 15A) and 1 μm (FIG. 15B)];

FIG. 16A, FIG. 16B, FIG. 16C, FIG. 16D, FIG. 16E, and FIG. 16F show the in vivo imaging of hepatic blood vessels and sinusoids. Scanning electron micrographs of murine hepatic tissue slices following injection of silicon microparticles. FIG. 16A: An open blood vessel surrounded by hepatocytes pseudo-colored in green. FIG. 16B: An RBC in the opening of a sinusoid. FIG. 16C and FIG. 16D show the two silicon particles (pseudo-colored in blue) engaged by cellular constituents lining the vessel wall;

In vivo cellular interactions with discoidal porous silicon microparticles. Microparticles were injected intravascularly into nude mice, followed 2 hrs' post injection by vascular perfusion and tissue collection. The boxed region of the hepatic blood vessel in the upper left image is show at increasing magnification in the succeeding scanning electron micrographs (bars 400, 30, 10, 5, 2 μm). A silicon microparticle is shown near the center of each image and is displayed in blue in the final image;

In vivo cellular interactions with silicon microparticles. High magnification scanning electron micrographs show diverse cellular constituents competing for a cationic silicon microparticle (left) and engagement of an anionic (oxidized) silicon microparticle by cells lining the vascular wall (right);

FIG. 17A and FIG. 17B shows the 2D-Gel analysis of particle binding proteome. FIG. 17A. Eluted proteins from OX-treated beads. FIG. 17B. Eluted proteins from APTES-treated beads. Spot key: 1—Ig light chain V region (clone 17s.2); 2—complement component 1q, C chain; 3—Ig light chain V region (clone 17s.2); 4, 5—alpha fibrinogen, polypeptide isoform 2; 6—apolipoprotein E; 7—apolipoprotein A; 8—anti-ds-DNA immunoglobulin light chain V region; 9—alpha fibrinogen, polypeptide isoform 2; 10—γ-fibrinogen; 11, 12—alpha fibrinogen, polypeptide isoform 2; 13—Ig light chain V region (clone 17s.2); 14—complement component 1q, B chain; 15—Ig light chain V region (clone 17s.2); 16—alpha fibrinogen; and FIG. 18 shows a cartoon schematic of one MSV delivered nanovaccine in accordance with one aspect of the present invention. Tumor antigens and adjuvants (TLR ligands and/or siRNA knocking down negative regulator of immune system) were formulated into nanoliposomes and loaded into MSV. Upon uptake of MSV particles by dendritic cells (both in vitro or in vivo), the MSV activated dendritic cells and promoted efficient antigen presentation to T cells, thus inducing strong immune responses.

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Hybrid particle vaccines are superior to single particle vaccines because they accomplish multiple synergistic tasks that are needed to elicit effective immune responses. The use of porous microparticles (such as porous silicon) permits_attachment of toll-like receptor ligand(s) (TLR-L) to the particle surface and loading with both antigens and immune-stimulating agents (for example, in the form of proteins, peptides, small molecules, RNA, DNA, and the like), either free or encapsulated in nanoparticles. The inventors have demonstrated that strategic placement of TLR-L on the surface of the outer-most particle leads to engagement of TLR on immune cells, resulting in: 1) enhanced particle uptake by immune cells [i.e., antigen presenting cells (APC), such as dendritic cells]; 2) activation of immune cells (i.e., increased expression of co-stimulatory molecules, cytokine secretion, and surface MHC expression on APC); and 3) enhanced migration of immune cells to the lymph node for activation of an immune response.

Others have shown that single particle vectors, such as PLGA or liposomes, can be loaded with antigens and TLR-L, however, the TLR-L is either introduced during particle fabrication, in which case it exists throughout the particle and a higher payload is needed to achieve sufficient surface density, or the ligand is attached to drug-loaded particles, which can lead to loss of the payload. The use of pre-formed porous particles permits selective attachment of TLR-L to the surface, followed by loading of the particle with antigens and cytokines by capillary action. It has been demonstrated (Tasciotti et al., 2008) that multiple secondary nanoparticles (e.g., carbon nanotubes and quantum dots) can be loaded into porous silicon microparticles simultaneously. The present invention provides compositions in which one or more antigens and one or more immuno-stimulants are loaded into the pores of TLR-L-labeled microparticles (either free, or e.g., encapsulated in secondary nanoparticles).

For example, nucleic acids such as DNA or RNA can be delivered in viral, chitosan, or PEI nanoparticles and polypeptides/proteins/peptides can be loaded into liposomes, micelles, or chitosan. Such nanoparticles can be fabricated in sizes that "fit" within the pores of a given microparticle, with the choice of nanoparticles dependant on factors, such as, without limitation, the nature of the payload(s) to be delivered, and the desired release kinetics of the active agent(s) contained therein.

Once internalized in cells, such microparticles are primarily contained within endosomes that eventually mature into acidic vesicles (see e.g., Ferrati et al., 2010). This acidification of endosomes is needed for antigen processing and presentation. It is within the acidic endosome that antigens are loaded into the cleft of major histocompatibility (MHC) molecules, which are then sent to the cell surface for presentation of antigen to other immune cells (T cells) in association the costimulatory molecules (e.g., CD80, CD86, CD40, and the like). Both expression of surface co-stimulatory molecules and diversion of MHC to the cell's surface are triggered by TLR activation.

The present invention has uniquely demonstrated that TLR-L coated porous silicon microparticles enhance migration of immune cells (DC) to the lymph node in a murine animal model. Data has revealed that the TLR-L labeled microparticles loaded with tumor antigens were able to slow the growth of tumors in mice bearing breast cancer xenografts (both preventative and therapeutic). It has been shown that liposomes bearing the commercial TGF-β inhibitor, LY364947, prevented tumor growth in a CRE-Elastase-RAS salivary gland tumor model. The inventors contemplate that the combined loading of tumor antigens and immune stimulants (e.g., TGF-β inhibitor or cytokines) in TLR-L labeled particles provide an effective vaccine that both initiates antigen-specific immune responses, and combats the immuno-suppressive microenvironment of tumors and tumor cell-infiltrated lymph nodes.

Figure 1:
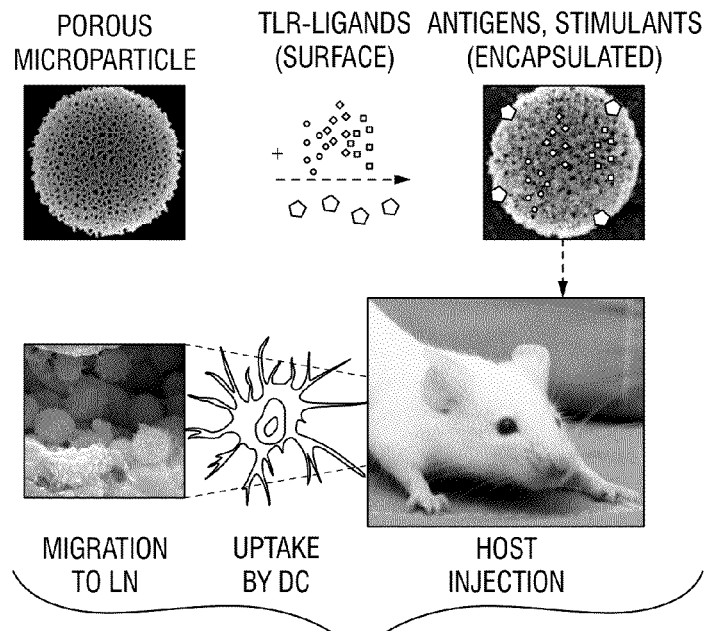
FIG. 1 shows a schematic showing assembly of the hybrid particle vaccine and introduction into a murine host, in accordance with one aspect of the present invention. Immune cells (blue) take up the hybrid particle vaccine and migrate to the lymph node where they present antigen to T cells to induce antigen-specific immune responses.
Figure 2A:
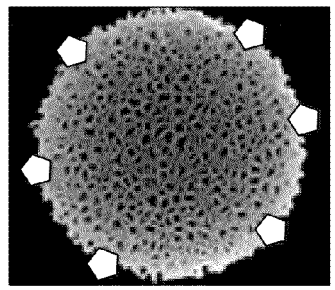
FIG. 2A is an electron micrograph showing a porous silicon particle with added objects in blue representing bound toll like receptor ligands (TLR-L) in accordance with one aspect of the present invention.
Figure 2B:
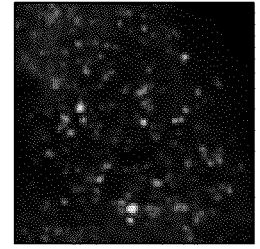
FIG. 2B and FIG. 2C are two photon microscopy images of a lymph node from a mouse that was injected with green T cells and red dendritic cells. They show localization of injected cells in similar regions of the lymph node.
Figure 2C:
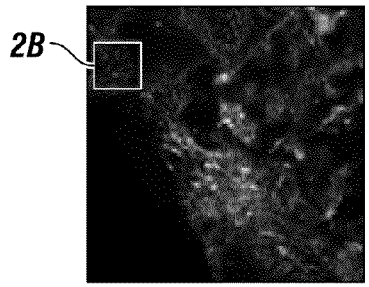
Figure 2D:
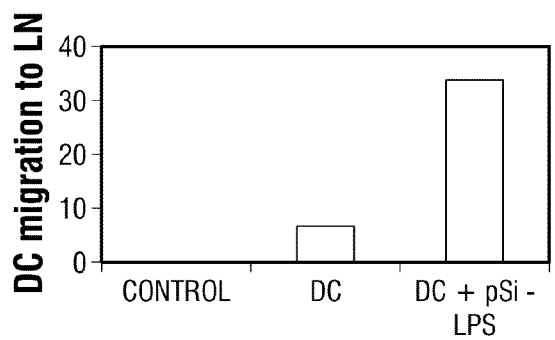
FIG. 2D is a graphical representation of the data comparing accumulation of untreated dendritic cells with accumulation of TLR-L bound microparticle treated dendritic cells in the lymph node (determined by flow cytometry identification of red labeled cells). Stimulation of dendritic cells (DC) with the TLR-L bound silicon particles increases their migration to the lymph node. Preincubation of DC with LPS and ova peptide-bound particles prior to injection in mice causes the DC to interact with T cells (cells are transgenic for the TCR that recognizes the OVA-MHC on the DC surface) in the lymph node. In a slice of the lymph node T cells appeared in green, and dendritic cells in red. Red DC surrounded by T cells (yellow for overlap), in an enlargement of the image (not shown)
Figure 3A:
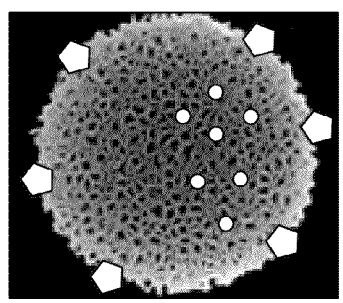
FIG. 3A, FIG. 3B, FIG. 3C and FIG. 3D show illustrative loading of tumor antigens (red) in a TLR-L labeled porous silicon particle (FIG. 3A) in accordance with one aspect of the present invention, in addition to particle labeling with TLR-L (blue). The graphs in FIG. 3B and FIG. 3C show tumor growth in mice implanted with bioluminescent breast cancer cells and the impact of the particle-based vaccine (i.e., TLR-L microparticle loaded with tumor cell lysate as the source of tumor antigens). In established tumors, the particle vaccine (red bars) have lower mean tumor growth (y-axis is number of days post injection with the vaccine).
Figure 3D:
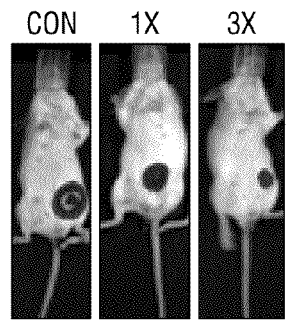
Figure 3B:
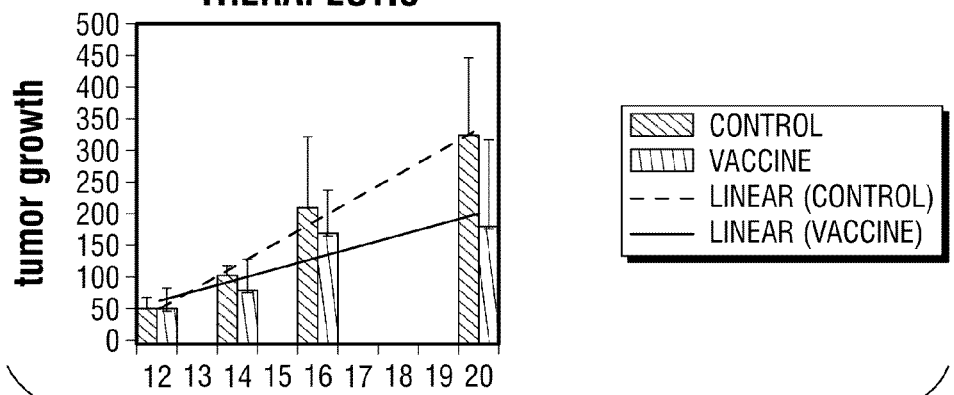
Figure 3C:
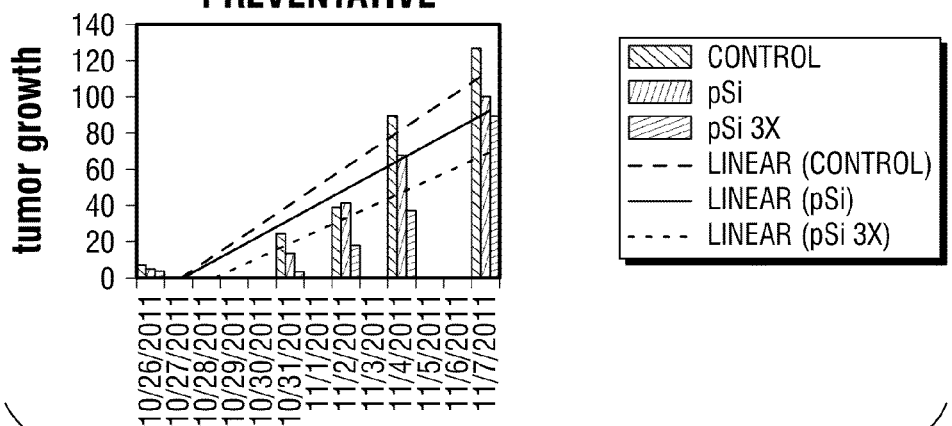

In FIG. 1, assembly of the hybrid particle vaccine is shown schematically, and introduction into a murine host is illustrated. Immune cells (blue) take up the hybrid particle vaccine and migrate to the lymph node where they present antigen to T-cells to induce antigen-specific immune responses.

In FIG. 2A-FIG. 2D porous silicon particles are shown with graphical representations of TLR-L (blue objects) on the particle surface. The particles were incubated with fluorescent immune cells, injected into mice, and the lymph node was imaged to demonstrate the location of injected cells within the lymph node (center images; DC labeled red and T cells green). The resulting graph showed the increase in migration of immune cells (DC) to the lymph node following incubation with particles (pSi) labeled on the surface with TLR-L.

In FIG. 3A-FIG. 3D, loading of tumor antigens (red) in a TLR-L labeled porous silicon particle is depicted (left). Data from two animal studies (center) showed that injection of this presentation of the vaccine reduces tumor growth when injected in established tumors (therapeutic) and prior to administration of tumor cells (preventative).

Figure 4A:
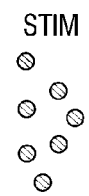
FIG. 4A, FIG. 4B, and FIG. 4C show an illustration depicting liposomes (FIG. 4A) loaded with the TGF-β inhibitor LY364947 (chemical structure shown in FIG. 4B; a commercially-available small molecule inhibitor), and their therapeutic effect on tumor growth (FIG. 4C) in accordance with one aspect of the present invention. The graph in FIG. 4C shows inhibition of salivary gland tumor growth by the drug (LY364947)-loaded liposomes. Liposomes have been shown to enhance porous silicon based therapeutics and the drug-loaded liposomes presented here are shown to result in decreased tumor growth following intravenous injection in mice bearing salivary gland tumors. Secondary nanoparticles such as liposomes have been shown to load into porous silicon particles and are the drug of choice shown is known to stimulate immune compromised tumor microrenvironments, leading to suppressed tumor growth. Induced refers to activation of a gene promoter that turns on a gene leading to tumor growth selectively in the salivary gland.
Figure 4B:
Figure 4C:
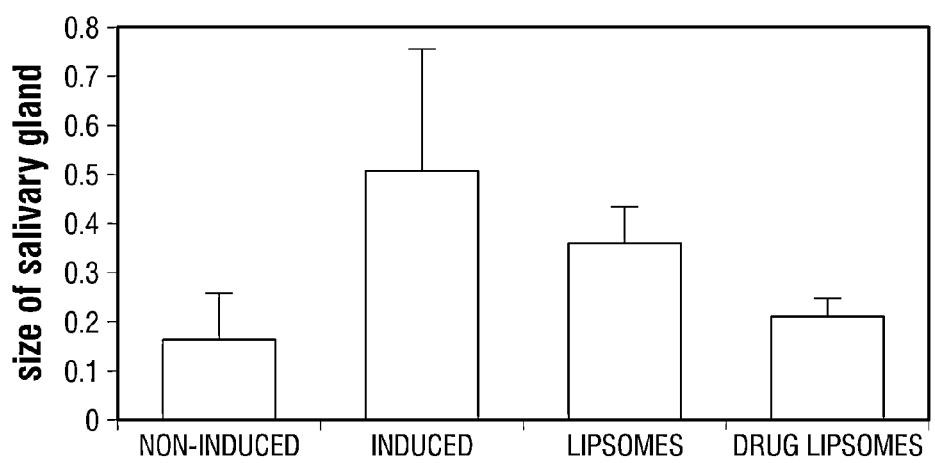
Figure 5A:
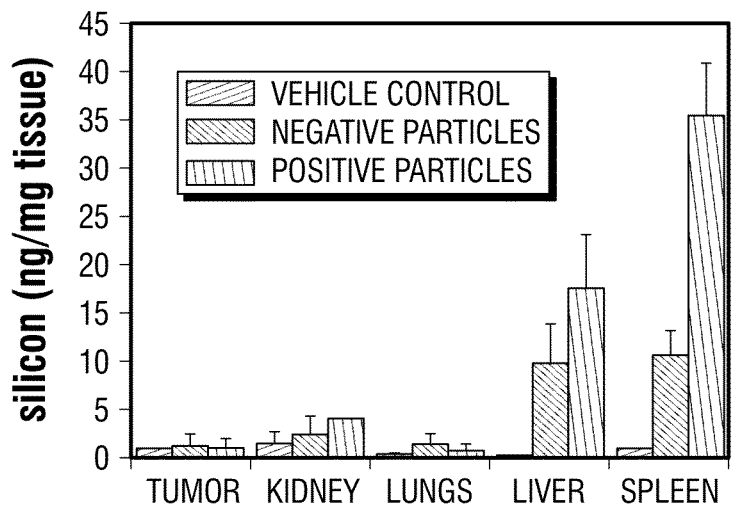
FIG. 5A and FIG. 5B show the in vivo biodistribution of silicon particles and particles located within macrophages in blood vessels. Positive and negative surface-charged silicon microparticles injected intravenously in mice accumulate predominately in the liver and spleen. ICP-AES analysis was done on mouse organs 24 hrs after injection of silicon microparticles to determine the amount of silicon in each organ and is presented in the graph as amount of silicon per mass of organ. A positive surface change enhanced microparticle accumulation in lymphatic tissue (i.e., spleen). The accompanying transmission electron micrographs show tissue slices taken from the liver of mice 24 hrs after intravenous injection of silicon microparticles. The silicon microparticles have been internalized by hepatic macrophages (Kupffer cells). Each tissue is presented at 10,000 and 60,000 magnification (bars=5 mm [FIG. 5A] and 1 mm [FIG. 5B])
Figure 5B:
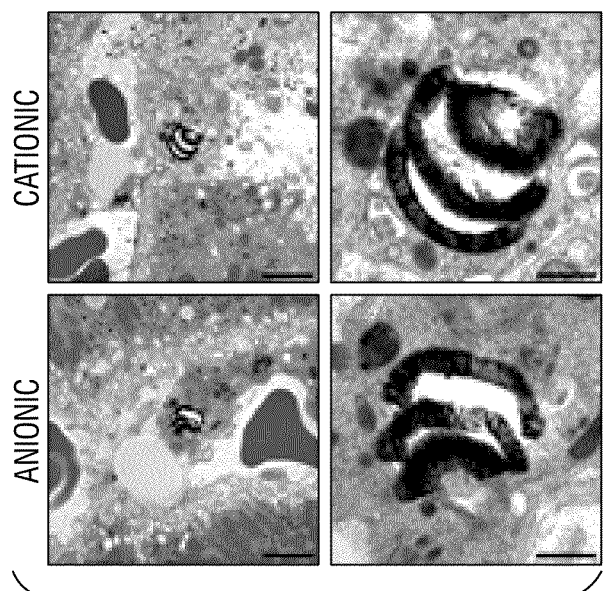
Figure 6A:
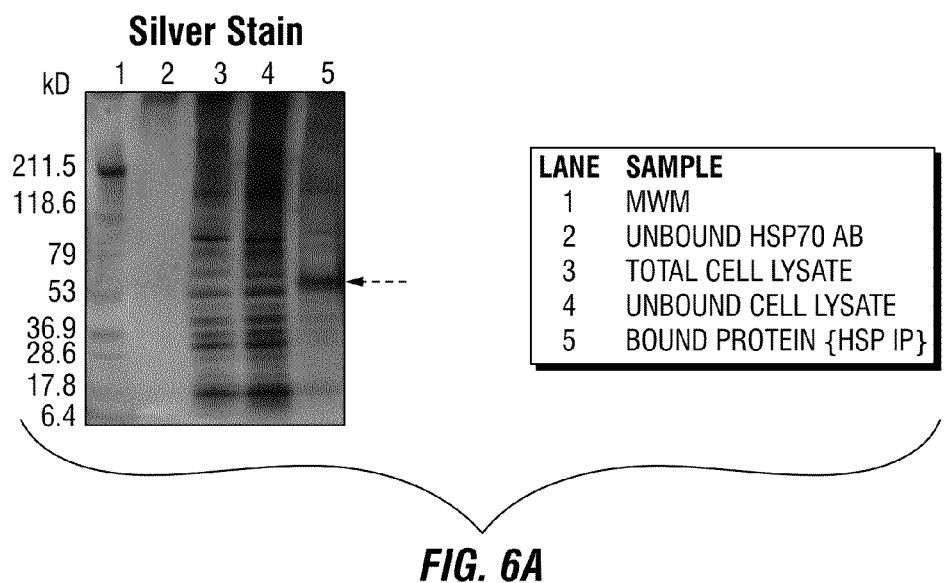
FIG. 6A and FIG. 6B show a silver stained gel and a Western blot, respectively, of proteins from mouse 4T1 tumor cells before and after enrichment with magnetic beads. The beads are labeled with an antibody that specifically binds to heat shock protein 70 (HSP70). A variety of heat shock proteins bind to mis-folded proteins and they are targeted clinically as sources of cancer antigens for vaccines. By use magnetic beads (i.e., iron oxide nanoparticles) to pull-down (i.e., isolate) HSPs and associated antigens from tumor cells for use in vaccines. These 'antigen-loaded' beads can be directed injected into patients or loaded into porous silicon microparticles in association with immune stimulants. The image on the left shows all proteins isolated from the tumor cells (lane 3), proteins form the cells that do not bind to the magnetic beads (lane 4), and proteins that bind to the beads (lane 5). The Western blot on the right is a replicate of the gel on the left, but only the size marker (lane 1) and proteins that bind to the anti-HSP antibody are visible. Lane 5 shows that the inventors have successfully enriched the sample for HSP. In addition to being directly injectable, it is anticipated that the use of magnetic beads will result in high levels of HSP-antigen complex isolation.
Figure 6B:
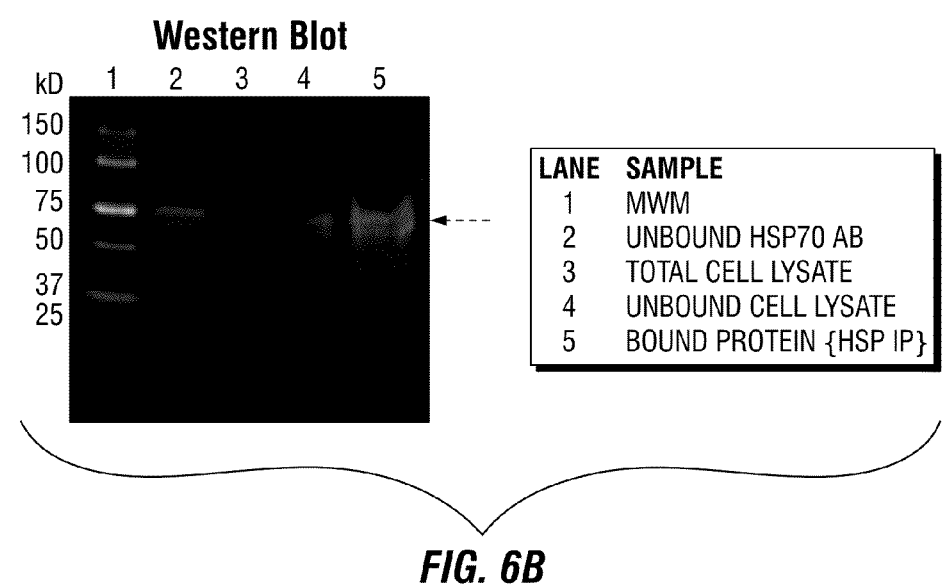
Figure 7A:
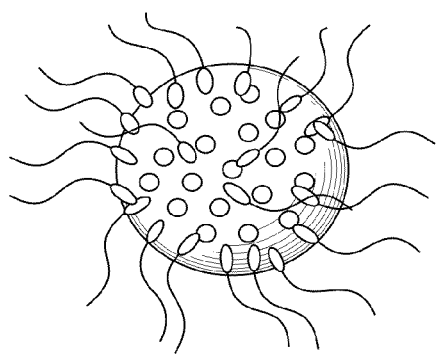
FIG. 7A, FIG. 7B, and FIG. 7C are drawings representing porous silicon particles bound by LPS (TLR-L) (FIG. 7A) and porous silicon particles bound by green fluorescent LPS (FIG. 7B). Fluorescent microscopy was used to validate conjugation of LPS to the microparticles by showing both unlabeled particles (top row) and green LPS labeling (bound) particles (bottom row) (FIG. 7C), supporting conjugation and/or adsorption of TLR-L to the surface of the particles.
Figure 7B:
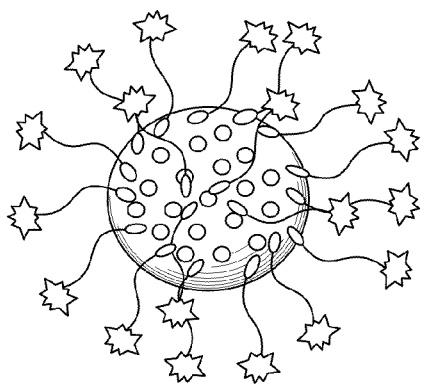
Figure 7C:
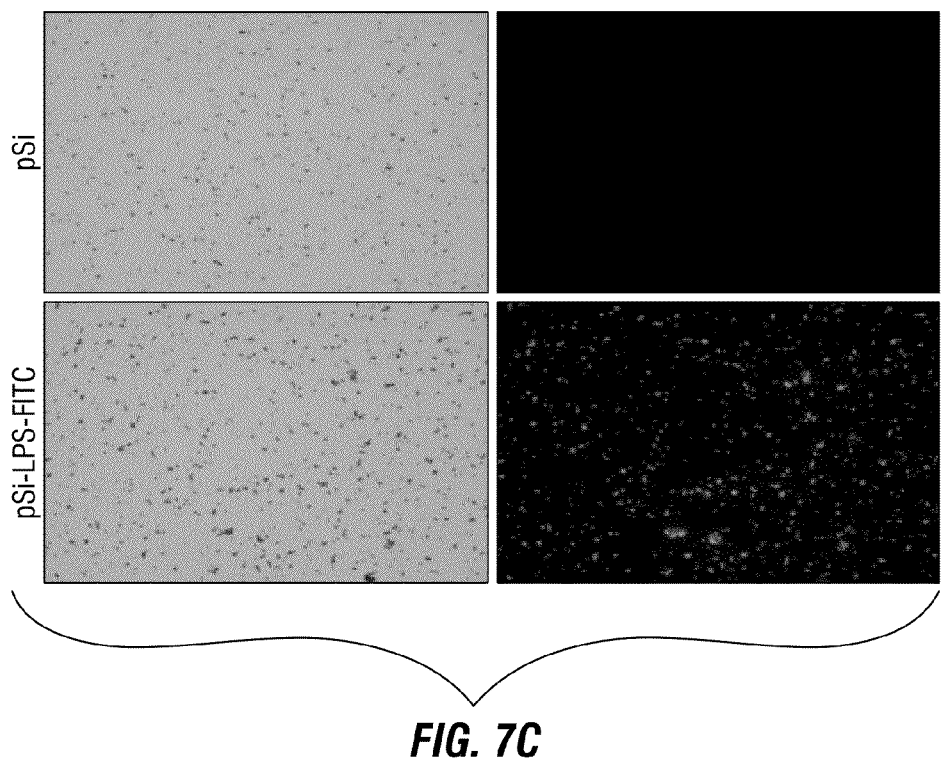
Figures 8A, 8B, 8C, 8D:
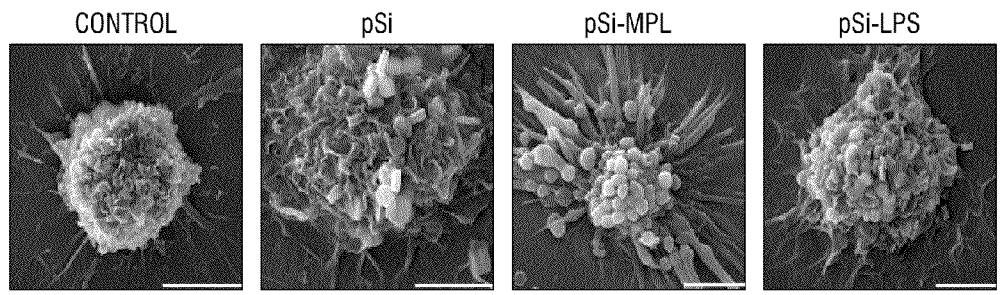
FIG. 8A, FIG. 8B, FIG. 8C, FIG. 8D, FIG. 8E, FIG. 8F, FIG. 8G, FIG. 8H and FIG. 8I show particle uptake by bone marrow DC was augmented by LPS/MPL conjugated pSi as compared with free pSi particles. The scanning electron micrographs (SEM) in FIG. 8A-FIG. 8H show early particle uptake by bone marrow-derived DC (BMDC). Confocal images (FIG. 8I) show enhanced particle uptake by MPL and LPS conjugated particles. Fewer cells are present in the pSi-LPS-treated group due to toxicity.
Figures 8E, 8F, 8G, 8H:
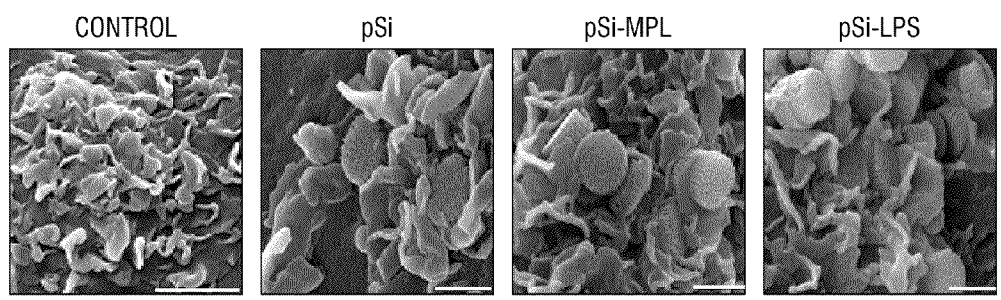
Figure 8I:
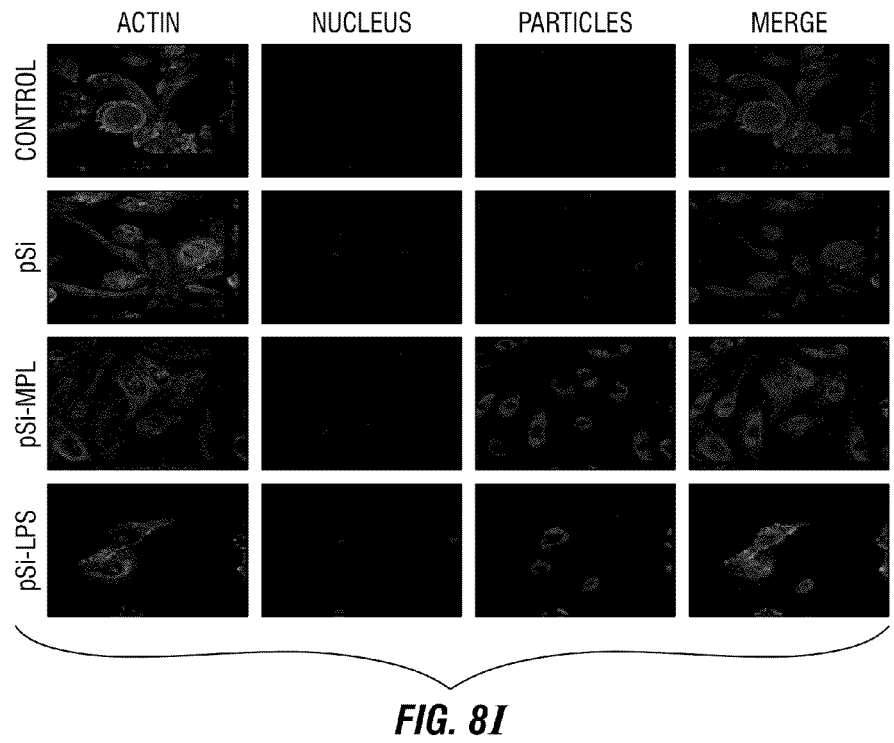
Figure 9A:
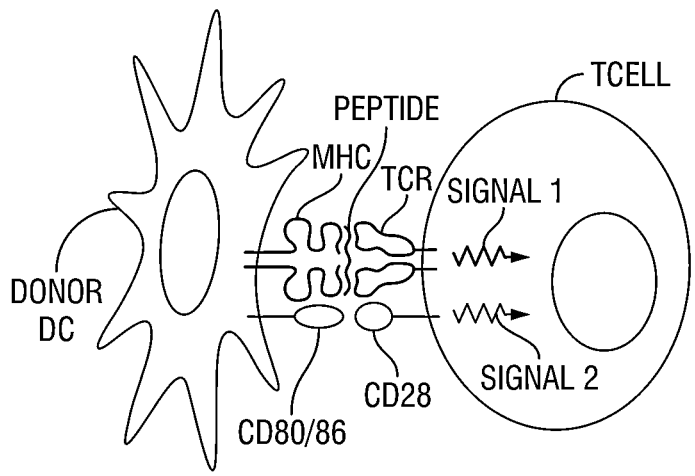
FIG. 9A, FIG. 9B, FIG. 9C, and FIG. 9D includes a drawing of a dendritic cell emphasizing key molecules involved in activating T cells (FIG. 9A), and demonstrates upregulation of these molecules (FIG. 9B, CD40, CD80 and CD86) following in vitro activation of the dendritic cells with TLR-L bound porous silicon microparticles (pSi-LPS and pSi-MPL) as measured using flow cytometry and fluorescent antibodies. MHC I (FIG. 9C) and MHC II (FIG. 9D) expression on dendritic cells were also increased by both pSi-LPS and pSi-MPL.
Figure 9B:
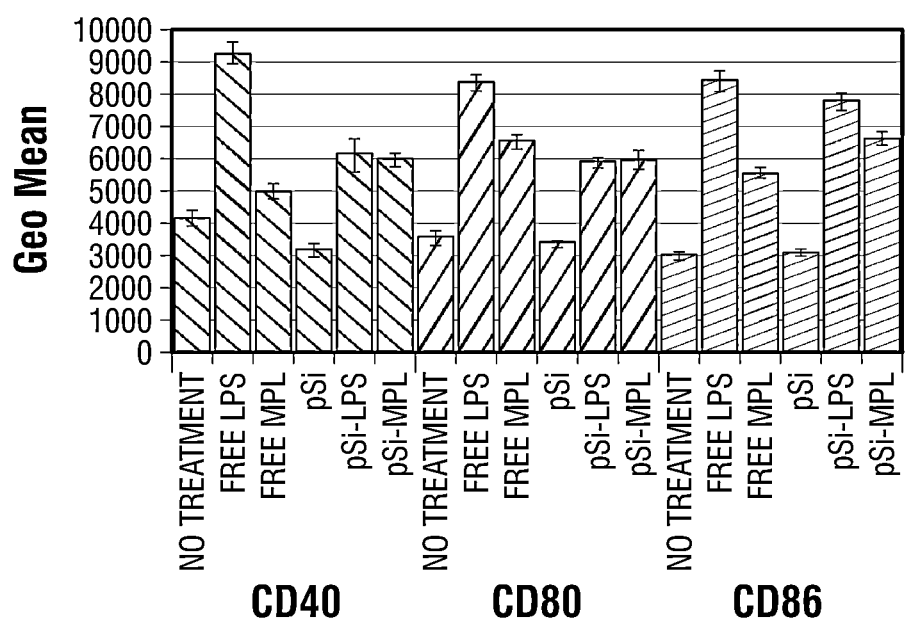
Figure 9C:
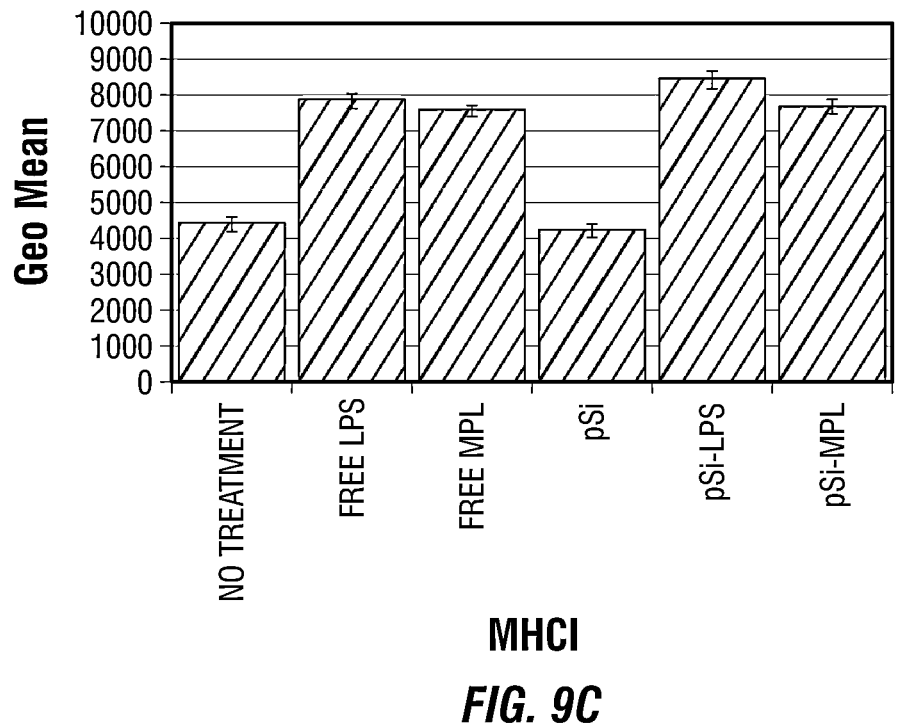
Figure 9D:
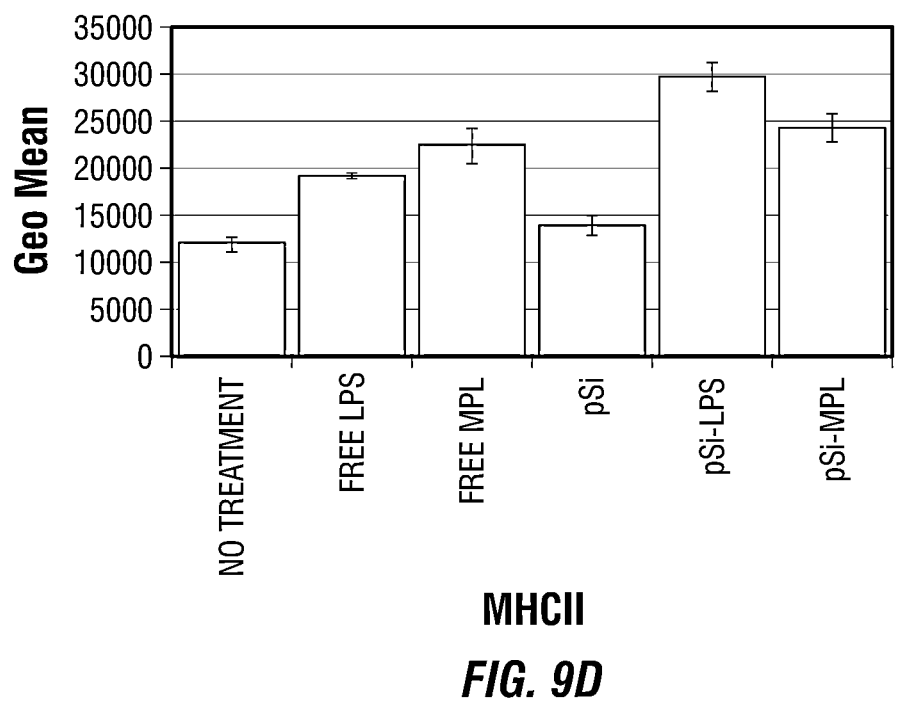

In FIG. 4A-FIG. 4C, liposomes (left; green) are depicted loaded with the TGF-β inhibitor LY364947 (center). The graph on the right showed inhibition of salivary gland tumor growth by the drug (LY364947)-loaded liposomes.

EXEMPLARY DEFINITIONS

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range. The term "e.g.," as used herein, is used merely by way of example, without limitation intended, and should not be construed as referring only those items explicitly enumerated in the specification. In accordance with long standing patent law convention, the words "a" and "an" when used in this application, including the claims, denotes "one or more."

Nanovector Taxonomy

A variety of nanocarrier-based drug delivery systems with different compositions, geometry, and surface modifications are under various stages of investigation (Ferrari, 2005; Wagner et al., 2006), producing an enormous collection of nanoparticles with a large array of possible combinations. First-generation nanovectors are the most elementary, and home to diseased sites by passive mechanisms such as the enhanced permeation and retention (EPR) effect, or more specifically, extravasate through gaps in tumor neo-vasculature. Avoidance of uptake by the RES is through functionalization with neutral polymers, such as poly(ethylene glycol) (PEG) (Hashizume et al., 2000; Maeda, 2001; Torchilin, 2005). Interactions between the aqueous environment and the hydrophilic polymers permits extension and mobility of the polymeric chains (Hrkach et al., 1997). Derivatized nanoparticles adsorb plasma components more slowly (Senior et al., 1991) based on steric repulsion forces (Owens, negating opsonin driven uptake of nanoparticles by phagocytic cells, and enhancing blood circulation time. Advantages of nanoparticle-based carriers include improved delivery of water insoluble drugs, prolonged circulation half-life, and reduced immunogenicity (Lee et al., 2005; Duncan, 2003).

The second category of nanovectors is comprised of delivery systems with an additional functionality (Brannon-Peppas and Blanchette, 2004; Kale and Torchilin, 2007; Farokhzad and Langer, 2009; Souza et al., 2009; Juweid et al., 1992), including: (a) targeting of the disease site through ligands that specifically bind to receptors uniquely- or over-expressed in the tumor microenvironment; (b) advanced functionalities, including co-delivery of multiple therapeutics or imaging agents, or triggered or controlled release of therapeutic agents. More sophisticated than their predecessors, the second generation of nanovectors represents a progressive evolution of first-generation nanovectors.

The third generation of nanovectors represents a paradigm shift in the strategy to overcome numerous obstacles encountered by nanovectors on their journey to the target site. Since no single agent can conquer the plethora of barriers that exist, these nanovectors are comprised of diverse families of nanoparticles nested into a single vector to achieve collaborative interactions. These carriers, or Logic Embedded Vectors (LEVs) (Ferrari, 2005), are therapeutic, multi-component constructs specifically engineered to avoid biological barriers, in which the functions of biorecognition, cytotoxicity and biobarrier avoidance are decoupled, yet act in efficacious, operational harmony. As an example of this therapeutic strategy, one can envision a vector which effectively navigates through the vasculature based on its geometry, attaches to the diseased vascular site through specific surface recognition and releases different nanoparticle payloads that simultaneously and synergistically extravasate, reach tumor cells and deliver their active agents at optimal concentrations to selectively eliminate malignancy with minimal side effects. This concept describes the multi-stage delivery system that will be extensively reviewed in this paper. By definition, third-generation nanovectors have the ability to perform a time sequence of functions through the use of multiple nano-based components that synergistically provide distinct functionalities.

In addition to the multi-stage delivery system, an example of third generation nanoparticles is biologically active molecular networks called "nanoshuttles", which are self-assemblies of gold nanoparticles within a bacteriophage matrix. Nanoshuttles combine the hyperthermic response of a near-infrared or radiofrequency external energy of the gold with the biological targeting capabilities of the 4C-RGD sequence presented by the phage (Souza et al., 2009; Juweid et al., 1992; Souza et al., 2006). These nanoshuttles collectively accommodate enhanced fluorescence, dark-field microscopy, and surface-enhanced Raman scattering detection.

Another example of a third generation nanovectors is the "nanocell", based on a disease-inspired approach to therapy (Sengupta et al., 2005). Utilizing the combinatorial chemotherapy approach, researchers have developed a nested nanoparticle construct that comprises a lipid-based nanoparticle enveloping a polymeric nanoparticle core called a "nanocell." A conventional chemotherapeutic drug, doxorubicin, is conjugated to a polymer core and an anti-angiogenic agent, combretastatin, is then trapped within the lipid envelope. When nanocells accumulate within the tumor through the EPR effect, the sequential time release of the anti-angiogenic agent, and then the cytotoxic drug, causes an initial disruption of tumor vascular growth and effectively traps the drug conjugated nanoparticle core within the tumor to allow eventual delivery of the cancer cell-killing agent.

Silica and silicon-based delivery systems represent the final example of third generation nanovectors. Mesoporous silica nanoparticles have been developed to co-deliver doxorubicin and Bcl-2 siRNA by encapsulation of doxorubicin inside the pores and complexation of siRNA in a dendrimer shell (Chen et al., 2009). The goal of this nanodevice is to simultaneously deliver an anticancer drug as an apoptosis inducer and siRNA molecules as suppressors of membrane pumps that mediate multidrug resistance. This multi-component nanodevice was able to significantly enhance the cytotoxicity of doxorubicin by decreasing the $IC_{50}$ 64-fold.

Mesoporous silicon devices include our multi-stage system (Tasciotti et al., 2008). Based on well-established semiconductor microfabrication lithography techniques, which allow for exquisite control of size, shape, and porosity, in concert with active biological targeting moieties, these vectors are intended to deliver large payloads of nanoparticles and higher order therapeutic and imaging agents to the tumor site. The "stage one" mesoporous silicon microparticles are designed based on mathematical modeling to exhibit superior margination and adhesion during their navigation through the systemic circulation. Stage one particles shoulder the burden of efficiently transporting, shielding, and controlling the rate of release of the nanoparticle payload. The encapsulated nanoparticles, called "stage two" nanoparticles, can be any nanovector construct within the approximate diameter range of about 5 to about 100 nm. The multi-stage drug delivery system is an example of LEVs which strategically combine numerous nano-components aimed at delivering single or multiple component nanovectors to the tumor site. The stage one particle is rationally designed to have a hemi-spherical or discoidal shape to enhance particle margination within the blood, as well as interactions between particles and endothelia, with a goal of maximizing the probability of active tumor targeting and adhesion [107]. In addition to improved hemodynamic properties and active biological targeting utilizing nano-components such as aptamers and phages, as will be discussed below, the stage one particles may also present specific surface modifications to avoid RES uptake. Following recognition of tumor vasculature and firm vascular adhesion, a series of nanoparticle payloads may be released in a sequential order dictated by diffusion from expanding or newly opened nanopores. Factors governing nanoparticle release include stage one particle degradation rates, polymeric coating, and stage two design strategies (e.g., environmentally sensitive cross-linking techniques with pH, temperature, and/or enzymatic triggers). It has been observed that the degradation rate of the porous silicon particles was proportional to its porosity, and it can be tuned from hours to days without surface functionalization. The versatility of this multi-stage delivery platform allows for a theranostic approach to therapy, including the delivery of chemotherapeutics, remotely activated hyperthermic nanoparticles, image contrast agents, and sequential, sustained release of successive stages of nanoparticle and active agents.

Rational Design of Stage-One Particles

The rational design of nanovectors aims at finding the dominating governing parameters in a series of events, which are encountered as the particle travels from the site of administration to the intended site of action. Multi-stage vectors are transported in the blood stream, interact with the vascular endothelium, and eventually interact with endothelia in the tumor neovasculature. These three fundamental events in the intravascular "journey" provide the basis for rational design, including: (1) the margination dynamics, (2) firm adhesion, and (3) control of internalization. The term 'margination' is used in physiology to describe the lateral drift of white blood cells and platelets from the center of the blood vessels towards the endothelial walls. The rational design of particles aims at generating a marginating particle that can spontaneously move preferentially in close proximity to the blood vessel endothelium (Decuzzi and Ferrari, 2008; Decuzzi and Ferrari, 2010).

Unlike spherical particles, non-spherical particles exhibit more complex motions with tumbling and rolling which can be exploited to control their margination dynamics without any need for lateral external forces. The longitudinal (drag) and lateral (lift) forces, as well as the torque exerted by flowing blood, depend on the size, shape, and orientation of the particle, as well as the stream direction and vascular changes that the particle encounters as it transverses through the bloodstream. For example, if one considers an elongated particle with an aspect ratio of 2, the particle motion becomes very complex with periodic oscillations towards and away from the wall (Decuzzi and Ferrari, 2008). Overall, however, the particle tends to approach the wall and periodically interact with its surface. More recently, in-vitro experiments conducted using spherical, discoidal and quasi-hemispherical particles with the same weight injected into a parallel plate flow chamber under controlled hydrodynamic conditions have shown that discoidal particles tend to marginate more than quasi-hemispherical particle, and both of these marginate more than spherical particles (Gentile et al., 2008; Gentile et al., 2008).

It was also shown that the probability of adhesion is decreased as a result of increasing shear stress at the vessel wall and particle size. Cellular adhesion increases as the surface density of ligand molecules on the particle surface and receptor molecules on the cell membrane increase. For all particle shapes, a characteristic size can be identified for which the probability of adhesion has a maximum (Lee et al., 2009). For example, hydrodynamic forces decrease as particle size decreases, but the area of interaction at the particle/cell interface is also reduced, leading to fewer ligand-receptor interactions and reduced potential to withstand even small dislodging forces. For larger particles, the number of ligand-receptor bonds increases, but so do the hydrodynamic forces on the particles. With respect to particle adhesion, rational design seeks to optimize binding strength by modulation of particle shape and a balance between ligand surface density and binding affinity.

There are different mechanisms in vivo that govern the behavior of particles. Recent studies have demonstrated that particles of different shape have unique biological distributions (Decuzzi et al., 2009). Six hours after systemic injection in mice, hemispherical particles accumulated preferentially in the liver, with minimal distribution to the heart and lungs, while discoidal particles showed relatively less retention in the liver, and high accumulation in the heart and lungs, as well as the spleen. Approximately 2% of the hemispherical particles accumulated in the tumor, which is significantly (Decuzzi et al., 2009) greater than 1 in 10,000 (0.01%) biomolecularly targeted therapeutic agents. Published in vivo studies support superior therapeutic efficacy of multi-stage delivered liposomal siRNA over first generation siRNA liposomes (Tanaka et al., 2010). In that work, a single injection of siRNA in a multi-stage construct resulted in gene silencing equivalent to six injections of liposomal siRNA delivered over three weeks. These findings suggested that higher level targeting was achieved by second-stage vectors and/or therapeutic agents, perhaps by means of sustained, long-term release of secondary agents from the first stage porous silicon vector.

There have been significant improvements in tumor accumulation (2-25 times higher) and therapy with PEGylated liposomal agents currently in clinical use as compared to non-sterically stabilized liposomes and to the free drug (Papahadjopoulos et al., 1991). However, numerous reports state that the main fraction of the drug still accumulates in the filtering organs, with therapeutic loss of the drug (Hong et al., 1999; Klibanov et al., 1990). With the multi-stage system, a comparable fraction of the multi-stage vector reaches the tumor; moreover, the fraction captured in the filtering organs is not therapeutically "lost." As demonstrated in the multi-stage siRNA therapy study, porous silicon carriers trapped in the filtering organs slowly released second stage particles that were then able to migrate to target tissue, efficiently suppressing tumor growth for more than 21 days.

Fabrication of Geometrically-Diverse, Stage-One Silicon Particles

First-stage nanoporous silicon particles are typically fabricated according to the edict of rational design for optimal performance, including: 1) Margination and adhesion; 2) loading with stage-two nanoparticles; and 3) control of degradation and release of secondary nanoparticles. Particles with determined size, shape and porous structure can be fabricated through a combination of photolithographic techniques and electrochemical etch (Serda et al., 2009; Tasciotti et al., 2009). A thin masking layer of SiN is deposited on the silicon substrate, followed by spinning for photoresist development. The photoresist is patterned with the desired photomask and the pattern is transferred into the substrate by dry reactive ion etch. The substrate is then selectively porosified according to the lithographic pattern by anodic electrochemical etch in a solution of hydrofluoric acid and ethanol to obtain porous silicon particles that can be released from the substrate. The resulting particle maintains a central nucleation site in the size and shape of the photolithographic pattern, surrounded by an external corona whose thickness is determined by the electrochemical etch. This straightforward process can be controlled at each step to fine-tune the physical properties of the resulting particle. Choosing the size and shape of the photolithographic pattern determines the size and shape of the particle nucleation site, influencing the overall size and shape. Particles have successfully been fabricated with a circular nucleation site of size ranging from about 400 nm to over 5 µm. The timing and gas composition of the dry reactive ion etch controls the depth and shape of the trenches formed in the silicon substrate, determining the aspect ratio and the profile of the resulting porous silicon particle. Shorter etch time creates shallow, high aspect ratio (up to 6) discoidal particles; while longer etch times yield thicker, quasi-hemispherical particles with aspect ratios ranging from 1 to 2. The substrate resistivity and doping type, timing, current density and solution composition during the electrochemical etch determine the thickness of the porous layer, the pore size and particle morphology (Serda et al., 2009; Tasciotti et al., 2009; Herino et al., 1987; Zhang, 2004). Increasing resistivity, larger currents, and higher concentrations of ethanol with respect to hydrofluoric acid all contribute to the increase in pore size. Pore size larger than 20 nm is associated with straight, un-branched pores, while pores in the 10-20 nm size range show a branched tree-like structure. Pores smaller than 10 nm yield a randomly-oriented network structure.

Loading Porous Silicon Particles with Second-Stage Nanoparticles

Pore size and morphology affect particle loading, payload retention, and release kinetics (Tasciotti et al., 2008). It has been shown that particles with 5 nm diameter pores can be loaded efficiently with 2×30 nm Single Wall Carbon Nanotubes (SWNTs), while 5-nm CdSe Quantum Dots (Qdots) were associated solely with the particle surface. Conversely, particles with 20 nm pores are capable of loading both SWNTs and the Qdots within the porous structure (Tasciotti et al., 2008). Sustained release of both Qdots and SWNTs from 20 nm pores has been demonstrated over the course of 24 hr.

Success at loading secondary nanoparticles into the porous silicon matrix is best achieved using dry silicon particles. Loading then occurs by adding a concentrated solution of nanoparticles that is pulled into the pores by capillary action, i.e., the incipient wetness method (Zhang et al., 2005; Boujday et al., 2007; Mellaerts et al., 2008). Optimization of loading takes into account pore size, dimensions of the payload, surface charge or functionalization, and solvent optimization.

Alternately, loading has been achieved by covalent attachment of nanoparticles to the silicon surface. Successful loading has also been demonstrated with 3-aminopropyltriethoxysilane (APTES) modified silicon microparticles and carboxylated iron oxide and gold nanoparticles using sulfo-N-hydroxysuccinimide and 1-ethyl-3-(3-dimethylaminopropyl) carbodiimide chemistry. Scanning electron micrographs showed quasi-hemispherical silicon microparticles covalently loaded with gold nanoparticles (6-nm core) before (top left) and after cellular uptake (top right). The accompanying 3-(4,5-dimethylthiazol-2-yl)-2,5-diphenyl tetrazolium bromide (MTT) proliferation assay showed similar rates of cell growth in the presence of control or gold loaded porous silicon particles at ratios of 5 and 10 silicon particles per cell.

Targeting

Advances in tumor targeting have turned Paul Ehrlich's once-outlandish concept of a "magic bullet," where malignancies in the body can be treated by chemical substances equipped with high affinity for that malignancy (Winau et al., 2004), into a very attainable goal. Thanks to significant strides in research concerning phage display libraries, it is now feasible to increase the affinity of nanoparticles for specific targets in these diseased states. This in turn results in increased amounts of nanoparticles concentrated at the site of action, permitting drug or imaging agents to exert their effects locally. In the case of targeted chemotherapeutics, enhanced efficacies result, and toxicity to healthy tissues and organs is substantially reduced. With regard to imaging agents, the increased amassing of nanoparticles at the site of action allows for enhanced contrast and proper delineation of tumor boundaries. In light of the overwhelming benefits of active targeting, the attachment of ligands to the surface of nanoparticles is presently an area of intense research. The ligands currently under active exploration, and those with the most clinical potential, include the following: peptides, thioaptamers, small organic compounds, carbohydrates, and antibodies.

During the process of angiogenesis and vascular remodeling in tumors, endothelial cells demonstrate an over expression of cell surface markers critical for cell proliferation and invasion, leading to lesion specific "zipcodes," or vascular addresses. These markers include several receptors and integrins, the principle ones being vascular endothelial growth receptor (VEGF) and the $\alpha_v\beta_3$ integrin (Pasqualini et al., 1997). Given their over-expression on the surface of tumor vasculature endothelia, as well as the fact that blood is in constant contact with endothelial cells, these receptors and integrins are very attractive markers for tumor targeting. Phage-display technology is used to map vascular zipcodes, that is, protein interacting sites. The benefits of phage technology include genetic manipulation, high throughput screening, and production in high titers (via propagation in host bacteria) (Decuzzi et al., 2009). Libraries of peptides are displayed on the surface of bacteriophage, then tested against target cells or in vivo, leading to isolation of target specific peptides by multiple rounds of "biopanning." Bound peptides are recovered and the sequence is screened against databanks to identify sequence homology with existing motifs. For example, the RGD-4C peptide, isolated by in vivo phage display, is currently being used as a tumor homing peptide for first stage vectors via targeting of integrins.

A cyclic Arg-Gly-Asp-D-Phe-Lys (cRGD) peptide has been successfully conjugated to the surface of polymer micelles that encapsulated superparamagnetic iron oxide nanoparticles (Khemtong et al., 2009); once administered intravenously, the polymer micelles were able to actively target A549 lung tumors implanted subcutaneously in mice, leading to enhanced tumor imaging under MRI as compared to non-targeted micelles.

Another option for targeting includes aptamers, oligonucleotide molecules that are selected based on their affinity for the native tertiary structure of target molecules expressed on the cell surface (Thiviyanathan et al., 2007). Modification of one or both of the phosphoryl non-bridging oxygen atoms of the aptamer with sulfur creates "thioaptamers" with increased resistance to nucleases, tighter binding, and reduced negative charge leading to enhanced cellular uptake of aptamers-decorated nanoparticles. The aptamers can be thio-modified enzymatically, and the resulting oligonucleotides have been shown to be rapidly cleared by the renal system. Hybrid thioaptamers, with a mix of thiophosphate and unmodified phosphate, are the best option for specificity, nuclease resistance, and high affinity.

A VEGF-toxin conjugate ($VEGF_{165}$-$DT_{385}$), administered intraperitoneally, was shown to be able to target a subcutaneous human ovarian cancer cell xenograft (MA148) in mice, leading to tumor growth delay (Olson et al., 1997), while a cationic polymer lipid-based nanoparticle fashioned with a small organic $\alpha_v\beta_3$ ligand has also been developed (Hood et al., 2002). After 24 hours, these nanoparticles, which also contained a gene encoding firefly luciferase, were observed in human melanoma cells over expressing $\alpha_v\beta_3$. Importantly, nanoparticles were rarely observed in healthy organs and tissues.

Folic acid represents a small organic molecule used for tumor targeting, given that the receptor for folic acid is a protein overexpressed in many different cancer cells (Weitman et al., 1992). Doxorubicin polymer micelles fashioned with folic acid showed increased uptake in KB cells in vitro, with in vivo work showing a significant decrease in tumor growth rate when compared to non-targeted micelles (Yoo and Park, 2004). Carbohydrate molecules have been used to target hepatocellular carcinoma, given the overexpression of the asialoglycoprotein receptor (ASGPR), a membrane lectin receptor, on these cells (Wands and Blum, 1991). Among the most-studied carbohydrate molecules for targeting are galactose and lactose. Cho et al. demonstrated a 30% increase in paclitaxel-loaded polymer micelles in cells overexpressing ASGPR as compared to cells that did not express the receptor (Jeong et al., 2005).

Monoclonal antibodies, which possess high binding affinities, are also actively being explored as tumor-specific targeting modalities. Trastuzumab, a humanized monoclonal antibody specific for the HER2/neu receptor (erbB2), is an FDA-approved drug used for the treatment of HER2-positive breast cancer (Tomadoni et al., 2004). Trastuzumab causes cell cycle arrest leading to decreased cancer cell proliferation and reduced angiogenesis. Antibodies specific for HER2 have been used as targeting ligands for selective delivery of silica gold nanoshells to tumor tissue (Carpin et al., 2010). Other antibody-based targeting agents include monoclonal antibodies specific alphavbeta3 (Wagner et al., 2010), which when covalently coupled to human serum albumin nanoparticles, resulted in enhanced binding to melanoma cells. Monoclonal antibodies against $\alpha_v\beta_3$ integrin were also shown to inhibit both cancer growth and angiogenesis (Wagner et al., 2010).

Therapeutic Applications of Multi-Stage Delivery Systems

Nanotechnology is projected to fill the gap between significant scientific advances in the areas of cancer imaging and diagnosis, discovery and development of a plethora of anticancer drugs, and their translation into improvements in cancer management. With optimal anticancer treatment regimens still lacking, novel therapeutic approaches are being explored to supplement or replace traditional gold standards, including surgical resection (Finlayson et al., 2003) and radiation therapy (Elshaikh et al., 2005). While the curative potential of anticancer drugs is indisputable, limitations that hinder clinical translation and success include nonspecific drug delivery. In this section, various "stage two" nanoparticles are described that may be successfully incorporated in a multi-stage system for various therapeutic applications.

Liposomes

Liposomes represent a nanotherapeutic modality that shows immense clinical potential for drug delivery. These vesicular nanostructures, formed from phospholipid and cholesterol molecules, possess several advantages for drug delivery. First, their inner hydrophilic compartment can encapsulate water-soluble drugs, as well as therapeutic proteins, DNAs, and siRNAs. Second, with a diameter in the range of 100 nm, the drug payload can be substantial. Lastly, their functionalizaton with PEG can grant them with stealth-like properties, avoiding uptake by the RES. The chief disadvantage to liposomal drug delivery is the inability to encapsulate poorly soluble drugs within the aqueous core, limiting encapsulation of drugs to the hydrophobic bilayer membrane. A PEGylated liposomal formulation, known as Doxil®, is currently in clinical trials for the treatment of Kaposi's sarcoma (Gabison, 2001). These stealth liposomes have long blood circulation times over non-PEGylated liposomes, and readily accumulate in tumors due to passive targeting (Kamaly et al., 2008; Zalipsky et al., 2007).

Another drug that was successfully encapsulated in liposomes is annamycin, a non-cross-resistant anthracycline (Booser et al., 2002). The pre-liposomal annamycin lyophilized powder contains phospholipids (dimyristoylphosphatidyl choline and dimyristoylphosphatidyl glycerol at a 7:3 molar ratio), annamycin (lipid:drug at a ratio 50:1 wt./wt.), and Tween-20. The surfactant in the formulation allows for better solubilization of the drug, shortening the reconstitution step, as well as a means to form nano-size carriers without destroying the liposomal structure (Zou et al., 1996). Similar to doxorubicin, the drug possesses native fluorescence in the red region. Flow cytometry data confirmed loading of annamycin liposomes into porous silicon microparticles. Loading resulted in a shift in the mean fluorescent intensity from 3 to 1285 AU. Other liposomal active agents that were successfully loaded into the multi-stage drug delivery system include paclitaxel, doxorubicin and siRNA.

Polymer Micelles

Ringsdorf and coworkers worked in the early 1980s on the development of polymer micelles as drug delivery vehicles (Gros et al., 1981). These spherical, supramolecular constructs, with a size ranging from 10-100 nm, are formed from the self-assembly of biocompatible amphiphilic block copolymers in aqueous environments (Savic et al., 2003; Matsumura and Kataoka, 2009; Nakanishi et al., 2001). The hydrophilic outer portion, typically composed of PEG, forms a hydrating layer, while the hydrophobic core, composed of polymers such as poly(D,L-lactic acid) (PDLLA), poly($\epsilon$-caprolactone) (PCL), and poly(propylene oxide) (PPO), houses the anticancer agent. The ability of the drug to be encapsulated within the hydrophobic core represents their main advantage, in addition to their innate possession of a PEG hydrophilic corona that prevents opsonization and RES uptake (Satomi et al., 2007), and their small size which leads to their preferential accumulation in tumor tissue through the EPR effect.

Currently, several polymeric micelle platforms are being explored in clinical trials. Kataoka and coworkers formulated doxorubicin-containing poly(ethylene glycol)-poly(L-aspartic acid) micelles (Nakanishi et al., 2001). This formulation, known as NK911, displayed long blood circulation times and nearly tripled the half-life of doxorubicin (Matsumura et al., 2004). Genexol-PM is another micelle formulation in clinical trials, and consists of PEG-PLA micelles that encapsulate paclitaxel. Findings showed that Genexol-PM was much more tolerable than the clinically used formulation of paclitaxel containing Cremephor® EL, a formulation that results in hypersensitivity reactions (Wiernik et al., 1987). As a result, the dose of paclitaxel administered to patients could be increased, which in turn resulted in enhanced anti-tumor efficacy in patients (Kim et al., 2004; Kim et al., 2004).

To further enhance selective delivery of chemotherapeutics to the lesion, doxorubicin and paclitaxel polymeric micelles have been loaded into the nanoporous matrix of the silicon microparticles. For doxorubicin the best loading was obtained with 1,2-distearoyl-phosphatidyl ethanolamine-methyl-poly(ethyleneglycol) anionic micelles loaded into oxidized porous silicon microparticles.

Biocompatibility

Directed Opsonization of Silicon Microparticles

The composition and physical characteristics of particles influences both their physical properties (Hirsch et al., 2003; Loo et al., 2004) (e.g., electromagnetic), and their biological attributes (Serda et al., 2009; Serda et al., 2009). Size, shape, chemical composition, and surface charge all strongly influence the impact nano- and micron-size particles have on cellular systems, leading to differences in biocompatibility. To explore the biological properties of our stage one porous silicon microparticles, the impact of particles of different sizes and surface modifications on interactions with macrophages and endothelial cells has been characterized.

For therapeutic and imaging applications, nanoparticles and microparticles may be administered intravenously. During transport in the blood stream, these particles become coated with serum components that adsorb to the particle surface. Associations between cells and particles are regulated in part by serum proteins adsorbed to the nanoparticle surface. These surface-bound components are referred to as either opsonins or dysopsonins, depending on their impact, which either favor or disfavor cellular binding and uptake. One method to reduce serum protein binding is to coat particles with a neutral polymer that reduces cellular uptake, such as PEG. A second strategy is to alter the particle surface to attract serum components that enhance binding to target cell populations (Serda et al., 2009).

As previously stated, the target of stage one nanoporous silicon microparticles is diseased vasculature. As previously discussed, during many pathological states, including cancer, inflammation alters surface moieties expressed on vascular endothelia. To simulate inflammatory conditions in vitro, endothelial cells were treated with TNF-α for 48 hr and the impact on cellular association with silicon microparticles was monitored by using the increase in orthogonal light scatter by cells upon association with particles as a metric for binding and cellular uptake. Serum components binding to oxidized silicon microparticles, as well as negatively charged polystyrene microparticles, inhibited particle association with endothelial cells, while factors binding to positive, APTES-modified silicon microparticles had no impact on microparticle association with endothelial cells. Stimulation with TNF-α further increased association of microparticles with endothelial cells. While opsonization of oxidized silicon microparticles with pure IgG similarly inhibited association with endothelial cells, it enhanced association with macrophages, which express receptors for immunoglobulin (e.g., FcγRII). These findings indicate that it may be possible to manipulate particle surface attributes to direct opsonization for selective targeting of cell populations.

Cellular Engulfment of Stage-One Silicon Microparticles

Benefits of cellular uptake of drug delivery particles include cell specific killing, molecular imaging, altered gene or protein expression, protein modification, and transcellular transport. Cellular uptake of nanoporous silicon microparticles has been explored using real-time confocal microscopy, scanning electron microscopy, and flow cytometry in two subclasses of endothelial cells, Human Umbilical Vein Endothelial Cells (HUVECs) and Human MicroVascular Endothelial Cells (HMVECs) (Serda et al., 2009). Initial experiments compared cellular uptake of labeled (Dylight-594; Pierce) versus label-free particles. Using flow cytometry-derived side scatter as a metric for cellular uptake of microparticles, cellular association with labeled particles was found to be equivalent to label-free particles. Similarly, labeling of cells with variable amounts of dyes (i.e., CellTracker Green; Invitrogen; 0.25-2 µM) did not impact cellular association with microparticles. Confocal imaging of a single cell demonstrated membrane expansion around a microparticle at approximately 5-7 min after particle contact with the cell (Serda et al., 2009).

To determine the kinetics for internalization of microparticles a double fluorescent/FRET based assay was developed (Serda et al., 2009). Intermolecular FRET was found to occur between FITC and PE fluorophores when FITC-labeled antibody, bound to the surface of endothelial cells, was coupled with a secondary PE labeled antibody. Emission from the FITC fluorophore is quenched upon binding of the secondary antibody, and cells appear positive for the PE fluorophore only. Cells with both surface-bound (quenched, PE positive) and internalized (protected; FITC positive) microparticles, are positive for both FITC and PE. Cells containing only internalized microparticles are green (FITC positive) only. Using the double antibody assay, the time for internalization of half of the microparticles was 15.7 min. Using flow cytometry to measure cellular association with microparticles in the presence of different ratios of particles to cells, cellular association was found to be identical for HUVECs at passages 5 and 8, and for HMVECs (Serda et al., 2009).

Cellular Compatibility of Stage-One Porous Silicon Microparticles

In order to validate the biological safety of therapeutic devices, it is essential to evaluate normal biological processes and the effect of devices on these events. The biological impact of porous silicon vectors has been evaluated in two cell lines representing the immune system (i.e., macrophages) and a potential physiological target or barrier to delivery (i.e., endothelial cells). Cellular morphology, cell viability, impact on cell cycle, mitotic potential and pro-inflammatory responses following cellular engulfment of silicon microparticles have been demonstrated (Serda et al., 2009). Both cell types internalize microparticles adhering to the cell surface by phagocytosis, with subsequent intracellular transport of vesicles to the perinuclear region of the cell (Serda et al., 2009). Mitotic partitioning of endosomes during cellular mitosis is an event mediated by cytoskeletal processes. It has been shown that endothelial cells with internalized silicon microparticles undergo normal cellular proliferation, and cells with as many as 30 internalized silicon microparticles display even partitioning of microparticle-bearing endosomes to daughter cells during mitosis (Serda et al., 2009). Completion of cytokinesis, the final stage of mitosis, was dependent on polarized delivery of endocytic recycling membranes, and the finding of polarized delivery of microparticle-bearing vesicles to daughter cells supports a non-disruptive role for internalized microparticles. The number of microparticles per cell was also monitored as a function of time over six days. At each cell doubling time for HMVECs (48 hr) the number of microparticles per cell was reduced by 50%, supporting equal partitioning of microparticle-bearing vesicles over multiple mitotic events (Serda et al., 2009).

Undisturbed endothelial proliferation and lack of cytotoxicity following internalization of silicon microparticles was also supported by an MTT assay, which measures mitochondrial enzyme activity. Control silicon microparticles and those covalently loaded with either iron oxide (10-nm core) or gold (6-nm core) nanoparticles did not alter cellular proliferation of endothelial cells over 72 hr. Similar data has also been obtained for macrophages.

The impact of silicon microparticle internalization on cell cycle has been evaluated in endothelial cells using flow cytometry (Serda et al., 2009). At 12 and 24 hr following microparticle introduction (10:1; microparticles:cell) DNA content, analyzed by propidium iodide staining, showed no difference in relative cell cycle composition compared to control cells. In contrast, cellular exposure to cis-platin, a common chemotherapeutic agent, inhibited cellular mitosis as evidenced by a reduction in the G2/M peak. Flow cytometry analysis of the apoptotic volume, that is, cells with cell volume loss or cell shrinkage, confirmed a major accumulation of cell fragments following cis-platin treatment, but no evidence of cell death due to cellular uptake of microparticles.

Since foreign material can elicit an immune response, induction of cytokine release following exposure of endothelial cells to silicon microparticles has been assessed by measuring two pro-inflammatory cytokines, IL-6 and IL-8, in the cell media. While positive control zymosan particles elicited a prominent increase in cytokine production, no significant increase was seen after microparticle exposure for 1, 4, and 24 hr. In summary, studies to date have shown that endothelial cells are unaffected by the presence of porous silicon microparticles based on analysis of cell morphology, viability, cell cycle, apoptosis, and mitosis. Similarly, macrophages display no impairment of cellular function in the presence of silicon microparticles based on cell morphology, viability, and inflammatory response.

Only spots exhibiting greater than 25-fold abundance in the APTES treated samples were included. "q-value" represented the false discovery rate (Storey and Tibshirani, 2003).

Porous Silicon Microparticles Exhibit Immunomodulatory Effects Leading to Suppression of Tumor Growth Nanoparticles, such as polymeric delivery platforms, can exhibit intrinsic immunostimulant properties, dependent on size, charge, surface modification, and composition. To function as effective adjuvants, a balance between immunostimulatory properties and biocompatibility is essential. The inventors have demonstrated that porous silicon (pSi) microparticles are effective delivery vehicles, with uptake by target cell populations. A peritonitis mouse model was used to access early innate immune responses 24 hours following administration of pSi microparticles. C57BL/6 mice were injected intraperitoneally with microparticles of various shapes and sizes and cytokine production and cell infiltration were assessed. pSi microparticles were found to have proinflammatory effects. The microparticles induced significant leukocyte infiltration into the site of injection and elevated IL-1β levels in lavage fluid.

As cancer progresses, immune responses become more tolerant and cancer cells become more refractory to chemotherapies. Select chemotherapeutics, including cyclophosphamide, doxorubicin, and paclitaxel, have immunodulatory effects. Based on the immunopotentiating effects of pSi microparticles, and the ability of monophosphoryl lipid A (MPL) adsorbed pSi microparticles to activate antigen presenting cells, the inventors have sought to potentiate the doxorubicin-mediated immune response through co-delivery of MPL-pSi microparticles. When tumors in mice bearing intramammary 4T1-luc breast tumors reached a volume of 100 mm³, mice were injected with doxorubicin loaded liposomes (5 mg/kg) and MPL-pSi microparticles (5×10⁸ microparticles; 10 µg MPL equivalent) by means of tail vein injection. Tumor growth was monitored by calipher measurements and luciferase expression using the IVIS Imaging System 200. While MPL-pSi microparticle-treated mice exhibited reduced tumor growth, mice receiving MPL-pSi microparticles and doxorubicin-loaded liposomes exhibited arrest of tumor growth. Thus pSi microparticles are an attractive immunopotentiating platform, with applications for both drug and antigen delivery.

EXAMPLES

The following examples are included to demonstrate illustrative embodiments of the invention. It should be appreciated by those of ordinary skill in the art that the techniques disclosed in these examples represent techniques discovered to function well in the practice of the invention, and thus can be considered to constitute preferred modes for its practice. However, those of ordinary skill in the art should, in light of the present disclosure, appreciate that many changes can be made in the specific embodiments that are disclosed, and still obtain a like or similar result without departing from the spirit and scope of the invention.

Example 1

Multi-Stage Delivery Nano-Particle Systems

Dendritic cell-based immunotherapy is currently in clinical trials for the treatment of cancer. Dendritic cells are the most potent antigen-presenting cells for the induction of T-cell immunity, making them promising targets for immunotherapy. Toll-like receptor (TLR) ligands have been proposed as vaccine adjuvants for boosting adaptive immunity in cancer therapy. TLR signaling induces dendritic cell activation that is characterized by enhanced expression of co-stimulatory molecules and increased secretion of cytokines necessary for activation and differentiation of naïve T cells (Ferrari, 2005). During evaluation of recent clinical studies, it became apparent that efficient DC-based immunotherapy is dependent on a number of factors, such as the mode of antigen loading, maturation of DC, injection site, and vaccination schedule (Theis et al., 2006; Riehemann et al., 2009; Jain, 1989). The major limiting factors for DC-based vaccines include insufficient loading of antigens by DC and the poor migratory capacity of DC to lymph nodes. For improvement of immunotherapy, nanotechnology provides unique opportunities for prolonged and shielded delivery of antigens and adjuvants to DC for antigen processing and presentation (Jain, 1999). This example shows the ability of TLR-ligated silicon microparticles to stimulate DC, become internalized, and enhance DC migration to the draining lymph node.

In this study, the inventors have tested the ability of porous silicon (pSi) microparticles to function as substrates for DC and to activate cells via engagement of surface TLR. One micron porous silicon discoidal micro particles, as well as particles surface decorated with TLR ligands, such as lipopolysaccharide (LPS) or monophosphoryl lipid (MPL), were presented to bone marrow-derived DC. The efficiency of particle up take and DC activation, based on surface expression of co-stimulatory molecules, major histocompatibility, and secretion of pro-inflammatory cytokines was studied, as well as the ability of particle-loaded DC to migrate to the draining lymph nodes. The impact of particle-conjugated TLR on these events is presented.

Materials and Methods

TLR ligands were conjugated to APTES-modified porous silicon microparticles using standard EDC cross-linking chemistry. Particle uptake was monitored using scanning electron microscopy (SEM) and confocal microscopy. Particle/endotoxin toxicity was evaluated by Annexin V staining of treated cells. DC marker expression was evaluated by flow cytometry. Cytokine secretion was measured by ELISA. DC migration to lymph nodes was examined by flow cytometry evaluation. Cytokine secretion was measured by ELISA. DC migration to lymph nodes was examined by flow cytometry evaluation of excised nodes.

Results

Confocal and scanning electron microscopy, as well as flow cytometry studies supported higher uptake of LPS and MPL conjugated particles. TLR ligands on the surface of particles induced morphological changes consistent with maturation to DC lineage.

Stimulated DC expressed elevated levels of co-stimulatory (e.g., CD80, CD86) and major histocompatibility molecules, and secreted pro-inflammatory cytokines both in vitro and in vivo. Ex vivo processed DC loaded with TLR ligand-coated pSi particles showed enhanced migration to lymph node as compared with control DC.

Example 2

Multifunctional Vector Cancer Vaccines

The present example describes the conjugation of 4T1 mouse-carcinoma plasma membrane proteins to iron oxide nanoparticles and co-loading of these nanoparticles into porous silicon or PLGA microparticles with either TNF-α or reporter expression vectors.

These multifunctional vectors were then either injected into BALB/c mice (or loaded into BALB/c-derived APCs ex vivo) for subsequent inoculation into mice. Trafficking of the vectors and imaging of lymphoid tissue was presented.

The introduction of nanoparticles to cancer vaccines provides a means of loading APC ex vivo and concurrently loading expression vectors for expression of cytokines to enhance APC maturation, migration, antigen processing, and surface expression of co-stimulatory molecules. Alternatively, the natural uptake or injected particles by phagocytic immune cells and subsequent cell-based trafficking of particles to lymphoid tissue presents a mechanism to bypass patient leukapheresis and ex vivo culturing of autologous APC, techniques currently used to produce cancer vaccines.

Example 3

TLR Ligand-Coated pSi Particles Stimulate Immune Cell Activation and Migration of Cells to Lymphatic Tissue Custom-made vaccines based on personalized tumor antigens are realistic options for secondary therapy, with the patient's excised tumor providing antigens. Overlap in the personalized repertoire of tumor antigens among patients also provides insight into targets for preventative cancer vaccines. Nanotechnology provides carriers for shielded delivery of antigens and presentation of immunostimulatory molecules. Rapid uptake of particles by phagocytic immune cells and migration to lymphatic tissue for antigen presentation provides opportunities to elicit tumor specific immune responses. Dendritic cells (DC) are the master antigen presenting cells (APC) for efficient processing and presentation of antigens. In this example, the inventors have tested the ability of mesoporous silicon particles (pSi) to function as substrates for DC and to activate cells via engagement of surface toll-like receptors (TLR), pSi particles, surface labeled with lipopolysaccharide (LPS) or monophosphoryl lipid (MPL), were presented to bone marrow-derived DC. This resulted in rapid uptake of particles, with an enormous capacity for number of particles internalized per cell. Confocal microscopy studies supported higher uptake of LPS and MPL conjugated as compared to unlabeled pSi, pSi particle uptake into DC was also supported by electron microscopy imaging. TLR ligands induced morphological changes in GM-CSF stimulated cells consistent with maturation towards a DC phenotype. As expected, LPS conjugation to particles resulted in significant toxicity. MPL conjugated pSi showed little or no toxicity to DC and showed improved particle uptake into DC with morphological changes consistent with maturation towards a mature DC phenotype. The impact of cytokine cocktail on DC maturation and its impact on particle uptake were also examined. Flow cytometry analysis supported greater uptake of pSi by DC stimulated with GM-CSF and IL-4 compared to GM-CSF alone, with reduced uptake in the presence of TNF-α. Consistent with findings reported by others, addition of TNF-alpha to the cell media also resulted in higher levels of expression of costimulatory molecules by DC, compared to cells stimulated with GM-CSF alone. Thus immature DC are better able to internalize particle-based vaccines, with cytokine or TLR-driven maturation enhancing expression of co-stimulatory molecules for more effective antigen presentation.

Lipid based TLR ligands such as LPS and MPL act as a potential adjuvant to enhance immunity. The present example provides LPS & MPL conjugated pSi particles for enhanced uptake of particles by immune cells and for sustained release of tumor antigens to activate immune cells to target cancer for cell killing. The ligands are conjugated to the surface of porous silicon particles (pSi) using standard conjugation chemistry. Data showed increased pSi particle uptake by dendritic cells (DC) when particles were surface labeled with TLR ligands and enhanced migration of particle-loaded cells to lymph nodes. This system provides a means for activating a patient's immune system to prime immune cells for processing and presentation of antigens.

Briefly, in this example, LPS and MPL were conjugated to the surface of APTES-modified porous silicon particles using standard conjugation chemistry. The ligand loading efficiency is determined by measuring ligand in solution before and after loading using absorbance. To further validate surface conjugation, association of fluorescent ligands to particles is measured by fluorescent confocal microscopy and using a fluorescent plate reader. Cellular uptake of TLR-labeled particles was shown to be increased compared to unlabeled particles using confocal and electron microscopy. Cellular activation by labeled particles was tested by evaluating cellular expression of CD80, CD86, CD40, MHCI and MHCII. Activation of DC following internalization of ligand-coated pSi particles was also confirmed by measuring cellular secretion of immune stimulatory cytokines such as TNF-α, IL-1β, and IL-6. Cell migration to lymph nodes was determined by measuring accumulation of fluorescent DC (DC were labeled, as well as particles).

The majority of vaccines use alum as an adjuvant, although alum is not immuno-stimulatory, and works (in part) via aggregation. pSi particles, however, offer a particular advantage, in that they are already micron-in-size, stimulate uptake by immune cells, and can be surface functionalized with one or more active ligands (such as TLR ligands). Moreover, the porous matrix of pSi particles can be loaded with pluralities of distinct antigens to elicit one or more target-specific immune responses.

Porous silicon particles are prepared by a silicon fabrication team. TLR ligands (labeled with FITC) were purchased from commercial vendors. BALB/c mice were used as a source to generate bone marrow dendritic cell (BMDC) using commercial GMCSF.

In illustrative embodiments, the inventors contemplate the use of such silicon nanoparticles labeled with TLRs to effect an increased uptake by dendritic cells, along with increased stimulation of immune response and significantly, increased migration. In addition to single "payloads," the present invention can also be adapted to include multiple payloads within single populations of nanoparticles (for example, an antigen and a tumor growth inhibitor), or even single or multiple payloads in mixed populations of nanoparticles within a given mesoparticle delivery vehicle.

Example 4

Proteomic Analysis of Serum Opsonins Impacting Biodistribution and Cellular Association of Porous Silicon Microparticles Mass transport of drug delivery vehicles is guided by particle properties, such as size, shape, composition and surface chemistry, as well as biomolecules and serum proteins that adsorb to the particle surface. In an attempt to identify serum proteins that influence cellular associations and biodistribution of intravascularly injected particles, two-dimensional (2-D) gel electrophoresis and mass spectrometry were used to identify proteins eluted from the surface of cationic and anionic silicon microparticles. Cationic microparticles displayed a 25-fold greater abundance of Ig light variable chain, fibrinogen, and complement component 1 compared to their anionic counterparts. Anionic microparticles were found to accumulate in equal abundance in murine liver and spleen, while cationic microparticles showed preferential accumulation in the spleen. Immunohistochemistry supported macrophage uptake of both anionic and cationic microparticles in the liver, as well as evidence of association of cationic microparticles with hepatic endothelial cells. Furthermore, scanning electron micrographs supported cellular competition for cationic microparticles by endothelial cells and macrophages. Despite high macrophage content in the lungs and tumor, microparticle uptake by these cells was minimal, supporting differences in the repertoire of surface receptors expressed by tissue-specific macrophages. In summary, particle surface chemistry drives selective binding of serum components impacting cellular interactions and biodistribution.

A prominent goal of intravascular delivery of therapeutic and imaging agents encapsulated in synthetic particles is site-specific delivery for greater therapeutic efficacy. Crucial to the success of these carrier systems is their ability to navigate through the bloodstream and across barriers as they journey to the site of action (Ferrari, 2010; Sakamoto et al., 2007). Particle attributes, such as size, shape, density, elemental composition, and surface chemistry greatly affect convective transport in the blood stream, margination, cell adhesion, selective cellular uptake, sub-cellular trafficking and tissue localization (Decuzzi et al., 2009; Gentile et al., 2008). As an example, particle composition and surface chemistry influence interactions with plasma constituents, which further impacts effective transport and desired cellular interactions (Campbell et al., 2002). As stated by Walczyk and colleagues, what a cell sees when it encounters a particle is the blood plasma-derived corona rather than the bare particle surface (Walczyk et al., 2010). A greater understanding of the impact of particle surface chemistry on biomolecular interactions will aid in creating particles with superior bio distributions.

The use of intrinsic particle properties as a driving force for cellular interactions and bio-barrier transport may prove superior to ligation of particles with targeting ligands, such as antibodies. The use of antibodies to drive cellular interactions favors uptake by macrophages of the reticuloendothelial system (RES), based on the high density of Fc gamma receptors on the surface of macrophages. Opsonization can also drive sequestering of particles by the RES, with the liver and spleen comprising the endpoint organs for the majority of particle-based injectables. This example defines the impact of particle surface chemistry on protein adsorption and the resulting cellular associations and biodistribution.

The concept of 'multi-stage carriers', wherein each stage (i.e. particle layer) performs part of the journey from the site of administration toward the target lesion has been discussed herein. Each stage adds a degree of targeting selectivity in the process. The platform consists of mesoporous silicon particles designed to shuttle higher level particles, and ultimately therapeutic and imaging agents (Taxciotti et al., 2008).

It is well known that bio-transport, cellular associations, and intracellular trafficking of drug delivery vehicles, as well as phagocytic engulfment of particles are driven in part by surface charge and the repertoire of macromolecules and plasma proteins that bind to the particle's surface. It was previously reported that, under serum-free conditions, both anionic and cationic porous silicon microparticles are phagocytosed by human umbilical vein endothelial cells (HUVECs) (Ferrari, 2010). However, in the presence of serum, only microparticles with an originally cationic surface are internalized.

Using quasi-hemispherical and discoidal silicon microparticles with either an oxidized, anionic surface, or an aminosilylated cationic surface, the study in this example sought to define plasma proteins adsorbing discriminately to the particle surfaces, and address how this potentially impacts cellular associations and biodistribution. It was hypothesized that different protein coronas would result in microparticle association with unique cellular populations based on affinities for different cell surface receptors, leading to disparate in vivo biodistributions. To identify serum proteins adsorbed to the particle surfaces bound proteins were eluted and two-dimensional gel electrophoresis (2DGE) and mass spectroscopy (MS) were used. The impact of particle surface charge on in vivo cellular associations and biodistribution was studied in an animal model of breast cancer. Endothelial and RES targeting based on particle surface chemistry-driven opsonization was explored by defining cellular interactions in the liver and spleen. Cellular associations of particles with the intraluminal surface of blood vessels were imaged by scanning electron microscopy, while transmission electron microscopy was used to image intracellularly localized particles. The data obtained herein enhances an understanding of the mechanics that drive in vivo trafficking of drug delivery vehicles.

Materials and Methods

Porous Silicon Microparticle Fabrication

Nanoporous quasi-hemispherical and discoidal silicon microparticles were fabricated in the Microelectronics Research Center at The University of Texas at Austin. The mean particle diameter, 3.2±0.2 µm, was determined using scanning electron microscopy and the average pore size, 26.3±13.6 nm (hemispherical) and 51.3±28.7 nm (discoidal)

was based on BET measurements. Briefly, heavily doped p++ type (100) silicon wafers (Silicon Quest, Inc, Santa Clara, Calif., USA) were used as the silicon source. For discoidal microparticles, a $SiO_2$ layer was thermally grown on the wafer, followed by a layer of silicon nitride (SiN) deposited by Low Pressure Chemical Vapor Deposition. Standard photolithography, dry etch of SiN in $CF_4$ plasma, and wet $SiO_2$ etch in 5% HF were used to transfer a pattern of 2 μm circular arrays on the silicon wafer. A three-step electrochemical etch was used to make silicon particles consisting of a low porosity mechanical stabilization layer, a large pore device layer, and high porosity release layer. The masking SiN and $SiO_2$ layers were removed in aqueous HF solution, and the silicon particles were released from the substrate by sonication in isopropanol. Details for creating hemispherical microparticles were recently published (Chiappini et al., 2010).

Surface Modification of Silicon Microparticles

An isopropyl alcohol (IPA) suspension containing silicon microparticles was transferred to a glass petri dish and the IPA was evaporated using a hotplate set at 60° C. overnight. The hotplate temperature was then raised to 120° C. for 15 min to ensure evaporation of residual IPA from the porous matrix. Dried microparticles were then treated with piranha solution (1 volume $H_2O_2$ and 2 volumes of $H_2SO_4$) with heating to 110-120° C. for 2 hour with intermittent sonication to disperse the microparticles. The microparticles were then washed three times and incubated in 10% nitric acid for 30 minutes. The microparticles were then washed in deionized water 3 times, followed by washing in IPA 3 times. For aminosilylation, oxidized microparticles were suspended in IPA containing 2% (v/v) 3-aminopropyltriethoxysilane (APTES; Sigma-Aldrich, St. Louis, Mo.) for 2 hours at 35° C., with mixing at 1300 rpm. APTES modified microparticles were washed in IPA, and the amine density was determined using a 4-nitrobenzaldehyde (NBA) colorimetric assay. Briefly, $2 \times 10^7$ APTES-modified microparticles were washed in coupling solution [0.8% glacial acetic acid in 99.2% anhydrous ethanol (Sigma-Aldrich)] 3 times and resuspended in 1 mL of reaction solution [5 mM NBA in coupling solution] for 3 hrs with mixing (900 RPM) at 50° C. Particles were then washed with absolute ethanol 5 times and resuspended in 1 ml of hydrolysis solution [0.14% glacial acetic acid in 50% ethanol]. Standards were prepared with NBA and absorbance was determined at 268 nm Microparticle concentration was determined using a Beckman Coulter Z Series Coulter Counter.

Zeta Potential Analysis

A ZetaPALS Zeta Potential Analyzer (Brookhaven Instruments Corp., Holtsville, N.Y.) equipped with a 90Plus/BI-MAS Multi Angle Particle Sizing Option was used to measure the zeta potential of particles suspended in 0.01M phosphate buffer at a concentration 1-50 μg/mL silicon. The impact of IgG and serum protein binding on microparticle surface charge was studied by incubating the microparticles ($1-3 \times 10^6$) in serum or pure IgG for 30 min at 4, 25 or 37° C. Measurements were performed at pH 5.0 and pH 7.4. IgG binding was measured based on fluorescent intensity of a secondary antibody. The secondary antibody was incubated with particles at 10 μg/mL, both before and after exposure to bare IgG.

Fourier Transform Infra-Red Spectroscopy (FTIR)

Microparticle samples were applied to the diamond surface of a SMART ATR attachment on a Nicolet 6600 FTIR Spectrometer (Nicolet Instrument Tech., Middleton, Wis., USA). The applied sample was then dried with nitrogen and the FTIR spectra were read. A room temperature detector was used to collect all data, and all readings were made using a resolution of 4 and averaging 16 readings in absorbance mode. Analysis of the peaks was performed using Omnic peak identification software and Microsoft Excel® software.

Scanning Electron Microscopy (SEM)

J774 macrophages, purchased from American Type Culture Collection (Manassas, Va., USA), were grown on 5×7 mm Silicon Chip Specimen Supports (Ted Pella, Inc., Redding, Calif., USA). Upon reaching 80% confluency, cells were incubated with silicon microparticles (1:10; cell:microparticle) for 15 min at 37° C. Samples were washed with PBS and fixed in 2.5% glutaraldehyde (Sigma-Aldrich; St. Louis, Mo., USA). After washing in PBS, cells were dehydrated with increasing concentrations of ethanol (30%, 50%, 70%, 90%, 95%, and 100%) for 10 min each. Cells were then incubated in 50% alcohol-hexamethyldisilazane (HMDS; Sigma-Aldrich) solution for 10 min followed by incubation in pure HMDS for 5 min to prepare for overnight incubation in a desiccator. Specimens were mounted on SEM stubs (Ted Pella, Inc.) using conductive adhesive tape (12 mm OD PELCO Tabs, Ted Pella, Inc.), and then sputter-coated with a 10 nm layer of gold using a Plasma Sciences CrC-150 Sputtering System (Torr International, Inc., New Windsor, N.Y., USA).

For SEM imaging of microparticles, samples were suspended in either IPA or water, then dried on ethanol washed SEM stubs (Ted Pella, Inc.) overnight in a desiccator. Micrographs were acquired under high vacuum, at 20-30 kV, spot size 3.0-5.0, using either a FEI Quanta 400 FEG ESEM or a Hitachi S-5500 high resolution SEM.

Tissue Electron Microscopy

For tissue SEM, at predetermined time points following intravascular injection of discoidal porous silicon microparticles ($1 \times 10^8$), animals were perfused by injection into the left ventricle with 30 mL of perfusion wash solution (Electron Microscopy Sciences, #1222SK) followed by 30 mL of perfusion fix solution (Electron Microscopy Sciences, #1223SK). Tissues were processed based on techniques adapted from Hashizume et al., 2000. Tissue was collected in fixative, followed by embedding in 3% agarose. Tissue sections of 100 μm thickness were cut using a Krumdieck MD-4000 Tissue Slicer (Alabama Research & Development, Munford, Ala., USA). Sections were rinsed with cacodylate buffer, immersed in cacodylate buffered 2% tannic acid for 24 hrs, washed twice with 0.2 M sodium cacodylate, then incubated in cacodylate buffered 2% osmium tetroxide for two hours at 4° C., and washed again in 0.2 M sodium cacodylate and dehydrated in increasing concentrations of ethanol, followed by infiltration with 100% t-butanol. Samples were dried in a dessicator, and then mounted on SEM sample stubs using carbon adhesive tape. Following sputter coating with a 10 nm thick layer of gold, samples were imaged using an FEI Quanta 400 FEG SEM.

Tissue TEM imaging was done on 100 nm sections of resin-embedded tissue using a JEOL 1200 transmission electron microscope at 60 kV with digital images collected using a 1 k×1 k Gatan BioScan camera Model 792.

In Vitro Microparticle Association Studies

HUVEC, purchased from Lonza Walkersville, Inc. (Walkersville, Md., USA), were cultured in EBM®-2 medium (Clonetics®, CC-3156; Lonza). Serum-free experiments used EBM®-2 medium (Clonetics®) supplemented with only hydrocortisone and GA-1000, plus 0.2% BSA. HUVECs were discarded after 7-8 passages. For flow cytometry studies, HUVECs ($1.5 \times 10^5$ cells/well) were seeded into 6-well plates and 24 hours later the cells were incubated with silicon microparticles (10-20 microparticles/cell) in the indicated media for 60 minutes. For opsonization experiments, microparticles were pre-incubated with 100 µl of serum or plasma on ice for 30 min. Stimulated cells were treated with TNF-α (10 ng/mL) and IFN-γ (100 U/mL) for 48 hrs prior to incubation with microparticles. Following cellular internalization, cells were washed with PBS, harvested by trypsinization and resuspended in PBS containing 1.0% BSA and 0.1% sodium azide (FACS wash buffer). Microparticle association with cells was determined by measuring side scatter using a Becton Dickinson FACSCalibur Flow Cytometer (Becton Dickinson; San Jose, Calif., USA) equipped with a 488-nm argon laser and CellQuest software. Data is presented as the percentage of cells associating with microparticles (percent of cells with high side scatter). Side scatter due to cells in the absence of particles was subtracted from the presented data. Sample populations were compared using a two-tailed distribution, two-sample equal variance t-test.

Animal Studies

Breast cancer xenografts were established in Crl:NU-Foxn1$^{nu}$ mice (Charles Rivers Laboratories International, Inc., Wilmington, Mass., USA) by intramammary injection of $1 \times 10^5$ 4T1 mouse mammary tumor cells (ATCC). After approximately 3 weeks, when the tumors reached 1 cm in diameter, mice were injected by tail vein with vehicle control (saline) or $1 \times 10^8$ 3.2 µm oxidized or APTES-modified silicon microparticles in 100 µl saline (n=3 mice per group). Twenty four hours after injection, the mice were sacrificed and tissues were excised and either frozen for immunohistochemistry or weighed, then moved to 5 mL of 80% 1M NaOH/20% EtOH for analysis of tissue biodistribution using inductively coupled plasma atomic emission spectrometry (ICP-AES).

Frozen tissues were sectioned and stained with antibodies specific for endothelia (anti-mouse CD34; Beckman Coulter, Fullerton, Calif., USA) or macrophages (anti-mouse CD204, scavenger receptor Type I/II; AbD Serotec, Raleigh, N.C., USA). CD34 was visualized using the STAT-Q Peroxidase (HRP) system and DAB, purchased from Innovex Biosciences (Richmond, Calif., USA). The secondary antibody used for the CD204 antibody was goat-anti-rat IgG:HRP (1:50 dilution; STAR72), purchased from AbD Serotec. Nuclei were stained with hematoxylin.

Tissue samples suspended in NaOH for ICP-AES were homogenized, placed on a tube rotator overnight, and then centrifuged at 4200 RPM (Beckman Coulter centrifuge). A 0.5-mL aliquot of the tissue slurry was moved to a conical tube with 4.5 mL of distilled water. Samples were analyzed for silicon using a Varian Vista AX at a power of 1 kW, with plasma flow set to 15 L/min, auxiliary flow of 1.5 L/min, and a nebulizer flow of 0.75 L/min, with 5 replicate readings at 15 seconds between each reading. A standard curve was generated using Fisher Scientific (Pittsburgh, Pa.) Silicon Reference Standard Solution.

Differential Protein Estimation by Two-Dimensional Gel Electrophoresis (2DGE)

Plasma was collected from 10 mice by orbital bleeding and placed in tubes containing ethylenediamine tetraacetic acid as the anti-coagulant. Following centrifugation at 1500×g for 10 min, the upper plasma layers were pooled and frozen. Prior to use, plasma was thawed on ice. Oxidized and APTES modified discoidal microparticles ($1 \times 10^8$; 0.5 mg each) were each incubated with 0.5 ml of plasma on ice for 30 minutes after vortexing. Microparticles were then washed 3 times with PBS, washed once in 0.1×PBS, and resuspended in 100 µL of Destreak Rehydration Solution (Fisher Scientific). Samples were vortexed, incubated at room temperature for 10 minutes, then centrifuged and the protein solution frozen at −80° C.

2DGE was conducted using Pharmacia's (GE Healthcare, Pittsburgh, Pa.) IPGphor multiple sample IEF device for the first dimension, and Bio-Rad's multiple gel SDS-PAGE systems (Protean Plus and Criterion Dodeca cells) for the second as first described by O'Farrell, 1975. Isoelectric focusing (IEF) was performed with 11 cm precast IPG strips (Bio-Rad, Hercules, Calif., USA). Sample aliquots were loaded onto dehydrated immobilized pH gradient (IPG) strips, and rehydrated overnight. IEF was performed at 20° C. with the following parameters: 50 Volts (V), 11 hours; 250 V, 1 hours; 500 V, 1 hours; 1000 V, 1 hours; 8000 V, 2 hours; 8000 V, 6 hours. The IPG strips were then incubated in 4 ml of Equilibration Buffer (6 M urea, 2% SDS, 50 mM Tris-HCl, pH 8.8, 20% glycerol) containing 10 µL/mL tri-2 (2-carboxyethyl) phosphine (Geno Technology, Inc., St. Louis, Mo.) for 15 min at 22° C. with shaking. The samples were incubated in another 4 mL of Equilibration Buffer with 25 mg/mL iodoacetamide for 15 min at 22° C. with shaking in order to ensure protein S-alkylation. Electrophoresis was performed at 150 V for 2.25 hr, 4° C. with precast 8-16% polyacrylamide gels in Tris-glycine buffer (25 mM Tris-HCl, 192 mM glycine, 0.1% SDS, pH 8.3). After electrophoresis, the gels were fixed (10% methanol, 7% acetic acid in ddH$_2$0), stained with SYPRO-Ruby (Lopez et al., 2000) (Bio-Rad), and de-stained in fixative. The de-stained gels were scanned at a 100-µm resolution using the Perkin-Elmer ProXPRESS 2D™ Proteomic Imaging System (Boston, Mass.) using 460/80 nm excitation and 620 nm (long pass) emission filters.

Measurement of Relative Spot Intensities

The 2D gel images were analyzed using Progenesis/SameSpots software (Nonlinear Dynamics, Ltd. Newcastle Upon Tyne, UK). Analysis relies on geometric correction of the scans and projecting them all into the same reference space, performing pixel-to-pixel matching, and then spot detection. Subsequent to automatic spot detection, spot filtering was manually performed and spots with an area of less than 250 pixels were filtered out, and spots with a volume (intensity)/area ratio of less than 150 pixels were also filtered. The matching of spots between the gels is manually reviewed and adjusted as necessary. In earlier work, it was shown that the log-transformed normalized spot volumes were normally distributed, indicating that nonparametric statistical comparisons such as t-tests could be applied to identify those proteins whose expression was significantly changed by treatment. A change in normalized spot volumes greater than ±25-fold was used to select spot that were subsequently robotically picked, trypsin-digested, and peptide masses identified by MALDI TOF. Protein identification was performed using a Bayesian algorithm (Zhang and Chait, 2000), where high probability matches are indicated by expectation score, an estimate of the number of matches that would be expected in that database if the matches were completely random. To determine gel-to-gel reproducibility, hierarchical clustering was performed by the hclust algorithm in the Splus statistical package (S-PLUS 6, Insightful Inc.), using Euclidian distance (Brasier et al., 2004).

Protein Identification

Protein gel spots were excised and prepared for MALDI TOF/TOF analysis using Genomic Solutions' ProPic II and ProPrep robotic instruments following the manufacturer's protocols. Briefly, gel pieces were incubated with trypsin (20 µg/mL in 25 mM ammonium bicarbonate, pH 8.0, Promega Corp.) at 37° C. for 4 hr. The 4800 MALDI TOF/TOF was used for peptide mass fingerprinting and sequence analysis and database interrogation. Data were acquired with an Applied Biosystems (AB) 4800 MALDI TOF/TOF and AB software package 4000 Series Explorer (v. 3.0 RC1) with Oracle Database Schema (v. 3.19.0) and data version (3.80.0)

to acquire both MS and MS/MS spectral data. The parameters used are included as supplemental material.

Results

Silicon Microparticles and Cellular Associations

Porous silicon microparticles were fabricated from silicon wafers using procedures that resulted in quasi-hemispherical (FIG. 12AA and FIG. 12B) or discoidal shapes (FIG. 12C). Previous in vitro studies show that both microparticle shape variants are candidates for cellular uptake by phagocytic cells (Serda et al., 2010). SEM images in FIG. 12B-FIG. 12C show microparticles on or near the surface of J774 macrophages. The mechanism of internalization has previously been shown to be actin-dependent phagocytosis and macropinocytosis (Serda et al., 2009). In FIG. 12D-FIG. 12F, a discoidal silicon microparticle is being internalized by a macrophage, and the formation of cellular filopodia can be seen both adhering to the microparticle surface and as a larger extension approaching the microparticle. It was previously shown that murine macrophages internalize both cationic and anionic silicon microparticles in the presence and absence of serum (Serda et al., 2009).

It was previously demonstrated that cellular uptake of porous silicon microparticles by human endothelial cells was altered by serum opsonins binding to the surface of microparticles in a charge dependent fashion (Serda et al., 2009). Cationic, aminosilylated silicon microparticles are internalized similarly in both serum-free and serum-containing media, however, internalization of anionic, oxidized silicon microparticles is reduced in the presence of serum proteins (Serda et al., 2009). The results in FIG. 13A-FIG. 13E summarize previously published findings in which serum proteins and pure IgG inhibit uptake of anionic silicon microparticles by endothelial cells, in the presence or absence of the inflammatory cytokines TNF-α and IFN-γ (Serda et al., 2009). The negative impact of serum biomolecules on microparticle uptake was greater in the presence of plasma compared to serum, and pre-opsonization of microparticles before addition to the cell culture did not alter uptake compared to adding non-opsonized microparticles to cells in the presence of media containing serum.

Microparticle Characterization and Serum Opsonization

Verification of microparticle surface modification was obtained using Fourier Transform Infra-Red (FTIR) spectroscopy (FIG. 13A). Oxidized microparticles exhibited a broad peak at 3350 cm$^{-1}$, indicating the presence of hydroxyl units. Aminosilylation of the microparticles introduced a broad peak near 3400 cm$^{-1}$ due to —NH stretching, and thereby supporting surface modification with amine groups. The presence of surface amines on aminosilylated microparticles was also demonstrated by detection of amines using a 4-nitrobenzaldehyde colorimetric assay (FIG. 13B). One milliliter containing $2 \times 10^7$ APTES-modified microparticles had an amine density of 0.35±0.004 mM.

The zeta potential, an indicator of surface charge, of silicon microparticles in the oxidized and aminosilylated state was −19.45±0.45 and 27.86±0.45 mV, respectively, in phosphate buffer, pH 5.0 (FIG. 13C). Incubation of microparticles with fetal bovine serum (FBS) across 3 temperatures for 30 min resulted in near neutral surface charges for both oxidized and aminosilylated microparticles in phosphate buffer at pH 5.0, with no major alterations caused by incubation at different temperatures.

At physiological pH (7.4) oxidized and APTES-modified microparticles had surface potentials of −25.7 and 6.3 mV, respectively. Exposure to IgG resulted in both subsets having similar, negative surface charges. Unlabeled IgG displayed a greater affinity for anionic compared to cationic (APTES) microparticles, based on flow cytometry measurements that compared binding of a secondary fluorochrome-labeled antibody to particles in the presence and absence of unlabeled primary antibody. Based on data showing that binding of the labeled secondary antibody (negatively charged) to unlabeled anionic microparticles was low, binding of the labeled secondary antibody to particles, following incubation with the unlabeled primary antibody, was predominately due to antibody-antibody interactions, providing quantitative insight into unlabeled antibody-particle interactions.

As reported previously, at physiological pH, the surface charge of serum-opsonized microparticles is negative for both oxidized and aminosilylated silicon microparticles (Serda et al., 2009). In contradiction to the belief that cationic particles enhance interactions with cell surfaces based on affinity to negative gylcocalx moieties, these data argue against surface charge as the explanation for selective endothelial binding and uptake of originally cationic microparticles.

Biodistribution of Cationic and Anionic Microparticles

A murine 4T1 model of breast carcinoma was used to study the biodistribution of silicon microparticles 24 hours after tail vein injection with $2 \times 10^8$ discoidal silicon microparticles (FIG. 14A). The study included 3 groups: vehicle control, cationic silicon microparticles, and anionic silicon microparticles (n=3 per group). ICP-AES analysis of silicon content (ng silicon/mg tissue) in excised tissue showed low levels of microparticles in tumor, kidney, and lungs. Anionic silicon microparticles were found in liver and spleen at similar concentrations (9.8 and 10.6, respectively), while cationic silicon microparticles showed preferential accumulation in the spleen compared to the liver (35.5 and 17.8, respectively; p<0.02; n=3). The spleen had significantly more cationic microparticles compared to anionic microparticles (p<0.002). While the reported lung accumulation of both cationic and anionic microparticles is low in this study, microparticle manipulations that cause aggregation increase lung accumulation drastically and make the lung the major organ for microparticle accumulation. These data are consistent with findings reported by Liu et al., 2009, in which hydrogel microparticles (1-5 microns) rapidly clear from the lung while nanoparticles (20-40 nm) have prolonged lung retention."

To determine if in vitro cell-type specific interactions also occurred in vivo, the impact of particle surface presentation on in vivo associations with endothelial cells and macrophages was examined (FIG. 13B). Liver and spleen tissues, harvested 24 hrs after microparticle injection, were labeled with antibodies specific for macrophage scavenger receptor (CD204) and for endothelial CD34. In the spleen, silicon microparticles were predominately located in the splenic cords and did not appear to associate with either endothelia or macrophages. Silicon microparticles were associated with macrophages in the liver, regardless of original surface chemistry, however, cationic microparticles were also found in association with hepatic vascular endothelial cells.

Based on ICP-AES data (FIG. 13A), accumulation of silicon microparticles was low in the lungs and tumor, despite high macrophage content. Immunohistochemistry analysis of tissues from mice injected with FITC-labeled silicon microparticles (anionic) supported heavy uptake by liver macrophages, with low macrophage uptake in the spleen and lungs (FIG. 14A). Thus, it appears that tissue-specific macrophages differ in their binding affinities for opsonized microparticles. This specificity may be driven in part by unique repertoires of cell surface receptors expressed by each macrophage tissue subtype. Tissue TEM images show both cationic and anionic silicon microparticles inside liver macrophages (FIG. 14B).

Cellular associations in hepatic blood vessels and sinusoids were examined by SEM 1-2 hours after injection of anionic microparticles. FIG. 15A and FIG. 15B (top left) show a scanning electron micrograph of an open blood vessel (pseudo-colored in red) surrounded by hepatocytes (green). The upper right image shows a red blood cell in the opening of a sinusoid. In the lower micrographs, anionic silicon microparticles (blue) can be seen attached to the vascular wall (shown at two magnifications). Cellular pseudopodia can be seen engaging the microparticles.

Hepatic tissue from mice injected with cationic silicon microparticles is shown in FIG. 16A-FIG. 16F. The boxed region of the blood vessel (top left image) is progressively magnified in the subsequent images. Among white blood cells is a cationic silicon microparticle. Cellular competition for the microparticle is seen between an endothelial cell, shown below the microparticle, and cellular constituents lining the vessel wall (seen above the microparticle). In the pseudo-colored image, endothelial cells are shown in red, lymphocytes in green, and the silicon microparticle in blue.

Identification of Serum Components Selectively Binding to Silicon Microparticles Silicon microparticles with opposable surface charges were incubated with murine plasma for 30 min, followed by washing with PBS, and removal of bound proteins using a protocol adapted from the National Cancer Institute's National Characterization Laboratory (NCL; www.ncl.cancer.gov). Proteins were separated by 2DGE and following automated spot detection proteins with normalized spot volumes greater than ±25-fold different between the two populations were subsequently robotically picked, trypsin-digested, and peptide masses identified by MALDI TOF. Using this criteria, 11 proteins were identified, all displaying higher selectivity for cationic microparticles. The proteins fell into three categories: (1) Ig light chain V region; (2) fibrinogen alpha polypeptide; and (3) complement component 1. Spots having the same protein ID are a common occurrence and may represent post-translational modification, including proteolysis.

Anionic microparticles were more selective in protein binding. None of the proteins eluted from the microparticles had spot volumes that differed by greater than 9-fold. Although not strikingly greater, there was selective binding of apolipoproteins A and E on anionic microparticles (FIG. 17A and FIG. 17B, spots 6 and 7), with 1.8 and 3.9-fold greater binding (ANOVA 0.962 and 0.218, respectively).

Discussion

Particle surface charge influences the extent and specificity of binding to serum proteins, which further regulates cellular associations and biodistribution. In vitro endothelial associations of anionic silicon microparticles are significantly reduced in the presence of plasma proteins or pure IgG. Conversely, cationic silicon microparticles continue to adhere to and be internalized by endothelial cells in the presence of serum. This is consistent with findings by Donald McDonald and colleagues (Thurston et al., 1998) who have demonstrated that cationic, but not anionic, neutral, or sterically stabilized liposomes associate with the luminal surface of tumor endothelial cells and are subsequently internalized. Marc Dellian et al. have also reported selective accumulation of cationic liposomes on vascular endothelium (Krasnici et al., 2003).

Three categories of proteins were identified absorbed to cationic silicon microparticles, fibrinogen alpha polypeptide, Ig light chain variable region, and complement component 1. Fibrinogen alpha polypeptide, a component of fibrinogen, is a blood-borne glycoprotein composed of three pairs of polypeptide chains. It is 644 amino acids and approximately 79 kDa. Various cleavage products of fibrinogen regulate cell adhesion and spreading, making fibrinogen-coated components likely candidates to regulate adhesion of particles to specific cell populations. Fibrinogen nanoparticles are reported to be internalized by L929 (murine fibroblast) cells (Rejinold et al., 2010), supporting a role for fibrinogen components in cellular adhesion and uptake.

Complement fragments bound to microorganisms promote leukocyte chemoattraction and phagocytosis. Various cell types have specific receptors for complement, with CR1 being the best characterized. C1 is a complex of three molecules, C1q, C1r, and C1s. C1r and C1s are proteases while C1q (460 kDa) binds to antigen-bound antibody via the Fc region, promoting binding to phagocytes (Kaul and Loos, 1993). Association of antibody and complement components to cationic silicon microparticles may thus favor interaction with professional phagocytes (i.e. macrophages), while binding to non-professional phagocytes (i.e. endothelial cells) may be mediated by the diverse combination of opsonins bound to the particle surface. The abundance of Ig and fibrinogen components adsorbed to cationic microparticles may also reflect non-specific entrapment of abundant serum components accompanying particle aggregation, which was observed during the PBS wash steps following incubation of cationic silicon microparticles with plasma.

It has been reported that "neutral" particles in serum have an outer protein corona consisting of fibrinogen, IgG, and albumin (Lundqvist et al., 2008). As just stated, both fibrinogen and Ig variable light chain were abundantly present on cationic silicon microparticles (albumin binding was not significantly different for the two particle surface variants). The zeta potential of unbound cationic silicon microparticles at pH 7.4 is approximately 6 mV. The low charge density may reflect the porous nature of the microparticles and may render the APTES-modified microparticles more similar to neutrally-charged particles than their nonporous counterparts. In contradiction to this finding, it was also shown by flow cytometry that IgG is preferentially adsorbed to anionic microparticles, or perhaps the data indicates that binding of unlabeled IgG to anionic microparticles orients the antibody in such a way the secondary fluorescent antibody binds more readily than it does to IgG-bound cationic microparticles. Atomic force microscopy analysis of porous silicon chips incubated with pure IgG, demonstrates binding of IgG to both cationic and anionic porous silicon (FIG. 17A-FIG. 17B). The presentation of immunoglobulin on the silicon chips is dissimilar and supports unique antibody binding orientations. Presentation of the Fc portion of the antibody on microparticles would be expected to inhibit uptake by endothelial cells, which express little or no Fc gamma receptors (Serda et al., 2009). A second explanation for the discrepancy in the data is that less IgG may bind to anionic microparticles in the presence of competing serum components.

Proteins bound to anionic microparticles include apolipoproteins A and E. Apolipoproteins bind to lipids to aid in their transport in the bloodstream and to provide an anchor to LDL receptors on target cells. Apolipoprotein A ranging in size from 419-838 kDa (Gaubatz et al., 1990), while Apolipoprotein E has 200 amino acids and is approximately 35 kDa (Rall et al., 1983). Apolipoprotein E consists of two domains, a lipid associating domain and a globular domain containing the LDL receptor binding site (Datta et al., 2000). The latter site is arginine-rich and may aid in the binding of ApoE to anionic silicon microparticles. The presence of Apolipoprotein E on the surface of anionic silicon microparticles may thus aid in delivery of microparticles to the liver.

Immunohistochemistry images of liver and spleen following intravascular administration of microparticles supported phagocytic uptake of both microparticle formulations by liver macrophages, as well as selective association of cationic microparticles with hepatic endothelial cells. A greater uptake of cationic microparticles was demonstrated in the spleen, compared to the liver. This may reflect lower levels of uptake of cationic, compared to anionic, microparticles by Kupffer cells in the liver and greater interaction with other classes of cells, including vascular endothelial cells. Scanning electron micrographs support competition of different classes of phagocytic cells for cationic silicon microparticles. Despite high macrophage content in the lungs, microparticles have been shown to predominately exist independent of lung macrophages and are present in low abundance. Based on these results, as well as the low tumor accumulation of microparticles, it appears that macrophage uptake of silicon microparticles is predominately restricted to liver Kupffer cells. Mechanisms that lower Kupffer cell uptake of microparticles may result in strategic localization of microparticles extracellularly, permitting sustained release of secondary nanoparticles, and ultimately therapeutic and/or imaging agents.

In summary, microparticle surface charge and serum opsonization of particles plays a major role in cellular associations, internalization, and biodistribution. Engineering drug delivery vectors for selective binding to serum components represents a mechanism to potentially direct cellular interactions and thus mass transport of therapeutic agents, as well as imaging agents and theranostics.

Example 5

Multistage Vector-Delivered Vaccine Containing Nanoliposome-Formulated Antigen and Adjuvants Conventional anticancer vaccines are limited by very weak in vivo immune responses, largely because of immunosuppressive tumor microenvironment and fast degradation of vaccine when injected in vivo. The present nanovaccine compositions incorporate TLR ligands to activate innate immune responses to reverse the suppressive microenvironment, and boost strong adaptive immune responses: Furthermore, multi-stage delivered nanovaccines provide protected and sustained release of vaccine, which induces long-lasting immune responses at a high magnitude.

The present example describes a nanotechnology-based vaccine formulation for the prevention and treatment of human cancers. The vaccine is composed of 1) porous silicon particles and 2) nanoliposomes loaded into the porous silicon. The nanoliposomes are packaged with one or more antigens (e.g., a protein or a peptide), and 2) one or more adjuvants such as innate immune activators (e.g., Toll-like receptor ligands, NOD-like receptor ligands, and/or siRNAs knocking down negative regulators of immune system). The vaccine is either directly injected into the body, or incubated with cultured dendritic cells followed by injection of the transformed dendritic cells into the body of the animal being treated. The prolonged release of antigen and adjuvants together from the porous silicon particles elicits strong immune responses to the antigen, and therefore provides vaccines at high magnitude and persistence. Depending on the antigen incorporated in the nanoparticles, the vaccine can be used for cancer immunotherapy, transplantation immunology and autoimmune disease management.

In illustrative embodiments, antigen(s) were formulated into nanoliposomes with or without the addition of one or more adjuvants (such as TLR ligands) and/or siRNAs knocking down negative regulators of immune system), and the resulted nanoliposomes were loaded into the pores of MSV particles (FIG. 18). The multistage vector (MSV) is comprised of two delivery carriers: (1) the degradable mesoporous silicon (also known as the first stage particle), and (2) a plurality of nanoparticles (also known as the second stage particles; e.g., liposomes) incorporated with one or more therapeutic agents (referred to as the third stage component (e.g., antigens and adjuvants) in the pores of the silicon particle. The loaded MSV particles were either directly infected into circulation for in vivo targeting of dendritic cells, or co-incubated in vitro with purified dendritic cells followed by injection of the primed dendritic cells into the body of the animal being treated. The resulting nanoparticles efficiently present the incorporated antigens to T cells by the dendritic cells, and the adjuvant in nanoparticles promoted dendritic cell activation and antigen presenting function. The antigen-specific immune responses could be monitored by checking T cell responses and antibody responses. The antitumor immunity has been determined with mouse models of melanoma and breast cancer.

Nano-Scale Delivery of TLR9 Ligand CpG into Dendritic Cells by Multi-Stage Silicon Vectors CpG is a short DNA oligonucleotide that contains unmethylated CpG sequences. It can activate TLR9 on endosomes and the subsequent immune responses in TLR9-expressing cells such as dendritic cells. CpG strongly activate dendritic cells and promote T cell responses, and has been used as an adjuvant in numerous clinical trials for cancer immunotherapy. However, currently CpG administration requires multiple injections and is associated with the risk of systemic inflammation or tolerance. Multistage silicon vector (MSV) is a unique delivery system that can deliver nano-scale payload into target tissues through stage 1 mesoporous particles and stage 2 nanoparticles carrying therapeutic agents, thereby achieving protected and sustained drug release. The MSV particles have been successfully used for in vivo delivery of siRNA and one injection induced significant knockdown of EphA oncoprotein expression for 2 weeks in a mouse model. Therefore, delivery of CpG by MSV systems may provide strong and sustained immune responses, and avoid side effect from repeated administration of soluble CpG. This was first tested on dendritic cells. As CpG has very similar structure as siRNA (20 nucleotide DNA vs. 21 nucleotide RNA), CpG-FITC was formulated into into liposomes following the procedure similar to siRNA formulation, and the liposomes were loaded into MSV particles, then the loaded MSV were co-incubated with mouse dendritic cells. Dendritic cells can efficient uptake these CpG-loaded particles as early as 1 hr after co-incubation, as evidenced by co-localization of green fluorescence and MSV particles inside the cells. Interestingly, by 3 hr after co-incubation, the FITC-labeled CpG started to be released from the MSV particles, and formed more diffused shape inside the cells, likely in the endosomes. Therefore, MSV can efficiently deliver liposome-formulated CpG into dendritic cells.

Multi-Stage Vector Delivered TLR Ligands Activates Dendritic Cells much Stronger than Soluble TLR Ligand TLR ligand can activate dendritic cells and promote dendritic cell maturation by upregulating the co-stimulatory molecule expression on dendritic cell surface, which is important for efficient antigen presentation to T cells. The inventors therefore tested whether MSV-particulated TLR ligand-containing liposomes could upregulate co-stimulatory molecules CD80 and CD86 expression on BMDCs. Both soluble and particulated CpG (400 ng/mL) strongly activated CD80 and CD86 expression on DCs. Meanwhile, low, dosage of soluble MPLA (20 ng/ml) and MPLA combined with CpG only weakly promote CD80 expression. Strikingly, MSV particulated MPLA and MPLA/CpG combination dramatically activate CD80 and CD86 expression. This result suggests that MSV-delivered TLR ligands strongly promote dendritic cell maturation.

Dendritic cells are a critical resource of interleukin 12 (IL-12), a key cytokine in innate immunity and type 1 T helper cell (Th1) responses. IL-12 production is tightly controlled in dendritic cells, and it requires a first priming signal from microbial ligands or interferon-γ and a secondary amplifying signal from CD40 ligand by T cells. Therefore, the integration of signals from pathogen, cytokines and T cells by dendritic cells mount the appropriate adaptive immune responses. Multiple TLR ligands combination can synergistically activate IL-12 production in dendritic cells. In preliminary studies, soluble MPLA and CpG did not induce IL-12 production in dendritic cells, but in sharp contrast, MSV particulated MPLA and CpG induced markedly increased IL-12 production, especially when MPLA and CpG were co-capsulated in MSV particles. The production of two other important proinflammatory cytokines, IL-6 and TNF-α, were also quantitated. Similar to IL-12, IL-6 and TNF-α, production is much higher in dendritic cells treated by MSV delivered single or combined TLR ligand, compared to that of soluble TLR ligand treatment. Thus, co-encapsulation of TLR ligands into liposomes and delivered by MSV system dramatically enhanced TLR ligand-induced dendritic cell activation.

Multi-stage vector-delivered tumor antigen elicited strong anti-tumor immunity in mouse melanoma model. TRP-2 is a tumor antigen derived from mouse B 16 melanoma, and strong anti-TRP-2 T cell responses would eliminate the B16 tumor growth engrafted on C571BL6 mice. However, direct injection of TRP-2 peptide only induced very weak immune responses, presumably because of peptide degradation and inefficient delivery to dendritic cells. In a significant study, the inventors primed purified dendritic cells with TRP-2 peptide only, or MSV particles only, or TRP-2 encapsulated inside MSV particles. After that, the primed dendritic cells were injected into mouse with B16 melanoma lung metastasis. After treatment, it was found that injection of dendritic cells primed with MSV-TRP2, but not MSV or TRP2, almost completely eradicated B 16 tumor metastasis on lung. These results suggested that liposomal antigen formulated inside MSV provided much stronger vaccine effect compared to antigen only.

The inventors have successfully formulated an antigen peptide derived from HER-2 protein into liposomes together with TLR ligands (MPLA for TLR4, CpG for TLR9). The resulting liposomes were then loaded into MSV particles and used to treat mouse dendritic cells with the MSV-loaded vaccine. The following observations were made: 1. Mouse dendritic cells can efficiently engulf these particles and the enclosed antigen and TLR ligands; 2. The TLR ligands encapsulated in the MSV strongly activate mouse dendritic cell surface protein expression, such as CD80, CD86, which are required for efficient antigen presentation to T cells; 3. The TLR ligands encapsulated in the MSV induced stronger proinflammatory cytokines release than that elicited by soluble TLR ligands. All of these indicated the resulting nanovaccine delivered by MSV was efficiently captured by dendritic cells and presented to T cells to subsequently induce very strong immune responses.

The nanovaccine described in this example formulates antigen and adjuvants together into nanoparticles (which simulate microbial particles at similar size) that can be captured by dendritic cells more efficiently than soluble antigen. The presentation of immune-stimulating adjuvants together with antigen prevents immune tolerance and promote antigen presentation. The resulting multistage vector system provided several layers of vaccine delivery, which ensured successful vaccine delivery to immune cells and eliciting strong immune responses.

REFERENCES

The following references, to the extent that they provide exemplary procedural or other details supplementary to those set forth herein, are specifically incorporated herein in their entirety by express reference thereto:

Adema, G J, et al., "Migration of dendritic cell based cancer vaccines: in vivo veritas?" *Curr. Opin. Immunol.*, 17:170-174 (2005).

Bachmann, M F and Jennings, G T, "Vaccine delivery: a matter of size, geometry, kinetics and molecular patterns," *Nature Rev. Immunol.*, 10(14787-796 (2010).

Ballester, M et al., "Nanoparticle conjugation and pulmonary delivery enhance the protective efficacy of Ag85B and CpG against tuberculosis," *Vaccine*, 29(40):6959-6966 (2011).

Bonifaz, L C et al., "In Vivo targeting of antigens to maturing dendritic cells via the DEC-205 receptor improves T cell vaccination," *J. Exp. Med.*, 199(6) (2004).

Booser, D J, et al., "Phase II study of liposomal annamycin in the treatment of doxorubicin-resistant breast cancer," *Cancer Chemother. Pharmacol.*, 50:6-8 (2002).

Boujday, S, et al., "Polyoxomolybdate-stabilized Ru(0) nanoparticles deposited on mesoporous silica as catalysts for aromatic hydrogenation," *Chemphyschem.*, 8:2636-2642 (2007).

Brannon-Peppas, L., and J O Blanchette, "Nanoparticle and targeted systems for cancer therapy," *Adv. Drug Deliv. Rev.*, 56:1649-1659 (2004).

Brasier, A R, et al., "Nuclear heat shock response and novel nuclear domain 10 reorganization in respiratory syncytial virus-infected A549 cells identified by high-resolution two-dimensional gel electrophoresis," *J. Virol.*, 78:11461-11476 (2004).

Caliceti, P and F M Veronese, "Pharmacokinetic and biodistribution properties of poly(ethylene glycol)-protein conjugates," *Adv. Drug Deliv. Rev.*, 55:1261-1277 (2003).

Campbell, R B, et al., "Cationic charge determines the distribution of liposomes between the vascular and extravascular compartments of tumors," *Cancer Res.*, 62:6831-6836 (2002).

Canal, P, et al., "Benefits of pharmacological knowledge in the design and monitoring of cancer chemotherapy," *Pathol. Oncol. Res.*, 4:171-178 (1998).

Carpin, L B, et al., "Immunoconjugated gold nanoshell-mediated photothermal ablation of trastuzumab-resistant breast cancer cells," *Breast Cancer Res. Treat.*, 125(1):27-34 (2010).

Chen, A M, et al., "Co-delivery of Doxorubicin and Bcl-2 siRNA by mesoporous silica nanoparticles enhances the efficacy of chemotherapy in multidrug-resistant cancer cells," *Small*, 5(23):2673-7 (2009).

Chiappini, C, et al., "Tailored porous silicon microparticles: fabrication and properties. *Chemphyschem.*, 11:1029-1035 (2010).

Datta, G, et al., "The receptor binding domain of apolipoprotein E, linked to a model class A amphipathic helix, enhances internalization and degradation of LDL by fibroblasts," *Biochemistry*, 39:213-220 (2000).

De Koker, S et al., "Designing polymeric particles for antigen delivery," *Chem. Soc. Rev.*, 40(1):320-339 (2011).

Decuzzi, P and M. Ferrari, "Design maps for nanoparticles targeting the diseased microvasculature," *Biomaterials*, 29:377-384 (2008).

Decuzzi, P and M. Ferrari, "Modulating cellular adhesion through nanotopography," *Biomaterials*, 31:173-179 (2010).

Decuzzi, P, et al., "Intravascular delivery of particulate systems: does geometry really matter?"*Pharm. Res.*, 26:235-243 (2009).

Decuzzi, P, et al., "Size and shape effects in the biodistribution of intravascularly injected particles," *J. Control Release*, 141(3):320-327 (2009).

Dostert, C et al., "Innate immune activation through Nalp3 inflammasome sensing of asbestos and silica," *Science*, 320(5876):674-677 (2008).

Duncan, R, "The dawning era of polymer therapeutics," *Nat. Rev. Drug Discov.*, 2:347-360 (2003).

Eisenbarth, S C et al., "Crucial role for the Nalp3 inflammasome in the immunostimulatory properties of aluminium adjuvants," *Nature*, 453(7198):1122-1126 (2008).

Elshaikh, M, et al., "Advances in radiation oncology," *Annu. Rev. Med.*, 57:19-31 (2006).

Evans, J, "Straight talk with . . . Mauro Ferrari," *Nat. Med.*, 15(7):716-717 (2009).

Farokhzad, O C and R. Langer, "Impact of nanotechnology on drug delivery," *ACS Nano.*, 3:16-20 (2009).

Ferrari, M, "Cancer nanotechnology: opportunities and challenges," *Nat. Rev. Cancer*, 5:161-171 (2005).

Ferrari, M, "Frontiers in cancer nanomedicine: transport oncophysics and logic embedded vectors," *Trends Biotechnol.*, 28(4): 181-188 (2009).

Ferrari, M, "Nanovector therapeutics," *Curr. Opin. Chem. Biol.*, 9:343-346 (2005).

Ferrati, S, et al., "Intracellular trafficking of silicon particles and logic-embedded vectors," *Nanoscale*, 2:1512-20 (2010).

Ellis, T et al.," Size-dependent immunogenicity: therapeutic and protective properties of nano-vaccines against tumors," *J. Immunol.*, 173(5):3148-3154 (2004).

Figdor, C G, et al., "Dendritic cell immunotherapy: mapping the way, *Nat. Med.*, 10:475-480 (2004).

Finlayson, E V, et al., "Hospital volume and operative mortality in cancer surgery: a national study," *Arch. Surg.*, 138:721-725; discussion 726 (2003).

Franchi, L and Núñez, G, "The Nlrp3 inflammasome is critical for aluminum hydroxide-mediated IL-1beta secretion but dispensable for adjuvant activity," *Eur. J. Immunol.*, 38(8):2085-2089 (2009).

Gabizon, A and Martin, F, "Polyethylene glycol-coated (pegylated) liposomal doxorubicin. Rationale for use in solid tumours," *Drugs*, 54(Suppl 4):15-21 (1997).

Gabizon, A A, "Pegylated liposomal doxorubicin: metamorphosis of an old drug into a new form of chemotherapy," *Cancer Invest.*, 19:424-436 (2001).

Gaubatz, J W, et al., "Polymorphic forms of human apolipoprotein[a]: inheritance and relationship of their molecular weights to plasma levels of lipoprotein[a]," *J. Lipid Res.*, 31:603-613 (1990).

Gentile, F, et al., "The effect of shape on the margination dynamics of non-neutrally buoyant particles in two-dimensional shear flows," *J. Biomech.*, 41:2312-2318 (2008).

Gentile, F, et al., "The margination propensity of spherical particles for vascular targeting in the microcirculation," *J. Nanobiotechnology*, 6:9 (2008).

Gentile, F, et al., "The transport of nanoparticles in blood vessels: the effect of vessel permeability and blood rheology." *Ann. Biomed. Eng.* 2, 36:254-261 (2008).

Godin, B et al., "Tailoring the degradation kinetics of mesoporous silicon structures through PEGylation," *J. Biomed. Mat. Res. A*, 2010:1236-1243 (2010).

Gordon, A N et al., "Recurrent epithelial ovarian carcinoma: A randomized phase III study of pegylated liposomal doxorubicin versus topotecan," *J. Clin. Oncol.*, 19(14): 3312-3322 (2001).

Gros, L, et al., "Polymeric anti-tumor agents on a molecular and on a cellular level," *Angew. Chem. Int. Edit.*, 20:305-325 (1981).

Harris, J M and Chess, R B, "Effect of pegylation on pharmaceuticals. *Nat Rev Drug Discov*, 2(3):214-221 (2003).

Hashizume, H, et al., "Openings between defective endothelial cells explain tumor vessel leakiness," *Am. J. Pathol.*, 156:1363-1380 (2000).

Heath, J R and M E Davis, "Nanotechnology and cancer," *Annu. Rev. Med.*, 59:251-265 (2008).

Herino, R, et al., "Porosity and pore size distributions of porous silicon layers," *J. Eectrochem. Soc.*, 134:1994-2000 (1987).

Hirsch, L R, et al., "Nanoshell-mediated near-infrared thermal therapy of tumors under magnetic resonance guidance," *Proc. Natl. Acad. Sci. USA*, 100:13549-13554 (2003).

Hong, R L, et al., "Direct comparison of liposomal doxorubicin with or without polyethylene glycol coating in C-26 tumor-bearing mice: is surface coating with polyethylene glycol beneficial?" *Clin. Cancer Res.*, 5:3645-3652 (1999).

Hood, J D, et al., "Tumor regression by targeted gene delivery to the neovasculature," *Science*, 296:2404-2407 (2002).

Hornung, V et al., "Silica crystals and aluminum salts activate the NALP3 inflammasome through phagosomal destabilization," *Nat. Immunol.*, 9(8):847-856 (2008).

Hrkach, J S, et al., "Nanotechnology for biomaterials engineering: structural characterization of amphiphilic polymeric nanoparticles by 1H NMR spectroscopy," *Biomaterials*, 18:27-30 (1997).

Hubbell, J A et al., "Materials engineering for immunomodulation," *Nature*, 462(7272):449-460 (2009).

Hutchison, S. et al., 2012. Antigen depot is not required for alum adjuvanticity. The FASEB Journal, 26(3), pp. 1272-1279.

Jain, R K, "Delivery of novel therapeutic agents in tumors: physiological barriers and strategies," *J. Natl. Cancer Inst.*, 81:570-576 (1989).

Jain, R K, "Transport of molecules, particles, and cells in solid tumors," *Annu. Rev. Biomed. Eng.*, 1:241-263 (1999).

Jeong, Y I, et al., "Cellular recognition of paclitaxel-loaded polymeric nanoparticles composed of poly(gamma-benzyl L-glutamate) and poly(ethylene glycol) diblock copolymer endcapped with galactose moiety," *Int. J. Pharm.*, 296:151-161 (2005).

Jordan, M. B. et al., 2004. Promotion of B Cell Immune Responses via an Alum-Induced Myeloid Cell Population. Science, 304(5678), pp. 1808-1810.

Juweid, M, et al., "Micropharmacology of monoclonal antibodies in solid tumors: direct experimental evidence for a binding site barrier," *Cancer Res.*, 52:5144-5153 (1992).

Kale, A A and V P Torchilin, "Smart" drug carriers: PEGylated TATp-modified pH-sensitive liposomes," *J. Liposome Res.*, 17:197-203 (2007).

Kamaly, N, et al., "Bimodal paramagnetic and fluorescent liposomes for cellular and tumor magnetic resonance imaging," *Bioconjug. Chem.*, 19:118-129 (2008).

Kaul, M and M Loos, "The Fc-recognizing, collagen-like C1q molecule is a putative type II membrane protein of macrophages," *Behring Inst. Mitt.*, 1993:171-179 (1993).

Kawai, T and S Akira, "TLR signaling," *Cell Death Differ.*, 13:816-825 (2006).

Khemtong, C, et al., "In vivo off-resonance saturation magnetic resonance imaging of alphavbeta3-targeted superparamagnetic nanoparticles," *Cancer Res.*, 69:1651-1658 (2009).

Kim, T Y, et al., "Phase I and pharmacokinetic study of Genexol-PM, a cremophor-free, polymeric micelle-formulated paclitaxel, in patients with advanced malignancies," *Clin. Cancer Res.*, 10:3708-3716 (2004).

Klibanov, A L, et al., "Amphipathic polyethyleneglycols effectively prolong the circulation time of liposomes," *FEBS Lett.*, 268:235-237 (1990).

Kool, M et al., "Alum adjuvant boosts adaptive immunity by inducing uric acid and activating inflammatory dendritic cells," *J. Exp. Med.*, 205(4):869-882 (2008b).

Kool, M et al., "Cutting Edge: Alum Adjuvant Stimulates Inflammatory Dendritic Cells through Activation of the NALP3 Inflammasome J. Immunol., 181(6): 3755-3759 (2008a).

Koshida, N and Koyama, H, "Visible electroluminescence from porous silicon. *Appl. Physics Lett.*, 60(3):347-349 (1992).

Krasnici, S, et al., "Effect of the surface charge of liposomes on their uptake by angiogenic tumor vessels," *Int. J. Cancer,* 105:561-567 (2003).

Lahoud, M H et al., "Targeting Antigen to Mouse Dendritic Cells via Clec9A Induces Potent CD4 T Cell Responses Biased toward a Follicular Helper Phenotype. *J. Immunol.*, 4-13 (2011).

Lee, C C, et al., "Designing dendrimers for biological applications," *Nat. Biotechnol.*, 23:1517-1526 (2005).

Lee, S Y, et al., "Shaping nano-/micro-particles for enhanced vascular interaction in laminar flows," *Nanotechnology*, 20:495101 (2009).

Less, J R, et al., "Interstitial hypertension in human breast and colorectal tumors," *Cancer Res.*, 52:6371-6374 (1992).

Liu, Y, et al., "Impact of hydrogel nanoparticle size and functionalization on in vivo behavior for lung imaging and therapeutics," *Mol. Pharm.*, 6:1891-1902 (2009).

Loo, C, et al., "Nanoshell-enabled photonics-based imaging and therapy of cancer," Technol. *Cancer Res. Treat.*, 3:33-40 (2004).

Lopez, M F, et al., "A comparison of silver stain and SYPRO Ruby protein gel stain with respect to protein detection in two dimensional gels and identification by peptide mass profiling," *Electrophoresis,* 21:3673-3683 (2000).

Lundqvist, M, et al., "Nanoparticle size and surface properties determine the protein corona with possible implications for biological impacts," *Proc. Natl. Acad. Sci. USA,* 105:14265-14270 (2008).

Maeda, H, "The enhanced permeability and retention (EPR) effect in tumor vasculature: the key role of tumor-selective macromolecular drug targeting," *Adv. Enzyme Regul.,* 41:189-207 (2001).

Majumdar, S and A K Mitra, "Chemical modification and formulation approaches to elevated drug transport across cell membranes," *Expert Opin. Drug Deliv.,* 3:511-527 (2006).

Manolova, V. et al., 2008. Nanoparticles target distinct dendritic cell populations according to their size. European Journal of Immunology, 38(5), pp. 1404-1413.

Marichal, T. et al., 2011. DNA released from dying host cells mediates aluminum adjuvant activity. Nat Med, 17(8), pp. 996-1002.

Martinon, F. et al., 2006. Gout-associated uric acid crystals activate the NALP3 inflammasome. Nature, 440(7081), pp. 237-241.

Matsumura, Y and K. Kataoka, "Preclinical and clinical studies of anticancer agent-incorporating polymer micelles," *Cancer Sci.,* 100:572-579 (2009).

Matsumura, Y, et al., "Phase I clinical trial and pharmacokinetic evaluation of NK911, a micelle-encapsulated doxorubicin," *Br. J. Cancer,* 91:1775-1781 (2004).

Matzinger, P, 1994. Tolerance, Danger, and the Extended Family. Annual Review of Immunology, 12(1), pp. 991-1045.

Matzinger, Polly, 2009. The Danger Model: A Renewed Sense of Self Science, 301 (2002).

McKee, A. S. et al., 2009. Alum Induces Innate Immune Responses through Macrophage and Mast Cell Sensors, But These Sensors Are Not Required for Alum to Act As an Adjuvant for Specific Immunity. The Journal of Immunology, 183(7), pp. 4403-4414.

Mehta, D and AB Malik, "Signaling mechanisms regulating endothelial permeability," *Physiol. Rev.,* 86:279-367 (2006).

Mellaerts, R, et al., "Physical state of poorly water soluble therapeutic molecules loaded into SBA-15 ordered mesoporous silica carriers: a case study with itraconazole and ibuprofen," *Langmuir,* 24:8651-8659 (2008).

Moghimi, S M and S A Davis, "Innovations in avoiding particle clearance from blood by Kupffer cells: cause for reflection," *Crit. Rev. Ther. Drug Carrier Sys.,* 11:31-59 (1994).

Nakanishi, T et al., "Development of the polymer micelle carrier system for doxorubicin," *J. Control Release,* 74:295-302 (2001).

Nembrini, C. et al., 2011. Nanoparticle conjugation of antigen enhances cytotoxic T-cell responses in pulmonary vaccination. Proceedings of the National Academy of Sciences, 108(44), p.E989, ÄiE997.

O'Farrell, P H, "High resolution two-dimensional electrophoresis of proteins," *J. Biol. Chem.,* 250:4007-4021 (1975).

Olson, T A, et al., "Targeting the tumor vasculature: inhibition of tumor growth by a vascular endothelial growth factor-toxin conjugate," *Int. J. Cancer,* 73:865-870 (1997).

Owens, D E, et al., "Opsonization, biodistribution, and pharmacokinetics of polymeric nanoparticles," *Int. J. Pharm.,* 307:93-102 (2006).

Palucka, A K, et al., "Taming cancer by inducing immunity via dendritic cells," *Immunol. Rev.,* 220:129-150 (2007).

Papahadjopoulos, D, et al., "Sterically stabilized liposomes: improvements in pharmacokinetics and antitumor therapeutic efficacy," *Proc. Natl. Acad. Sci. USA,* 88:11460-11464 (1991).

Pasqualini, R, et al., "Alpha v integrins as receptors for tumor targeting by circulating ligands," *Nat. Biotechnol.,* 15:542-546 (1997).

Rall, S C, Jr., et al., "Identification of a new structural variant of human apolipoprotein E, E2(Lys146 leads to Gln), in a type III hyperlipoproteinemic subject with the E3/2 phenotype," *J. Clin. Invest.*, 72:1288-1297 (1983).

Randolph, G. J. et al., 1998. Differentiation of Monocytes into Dendritic Cells in a Model of Transendothelial Trafficking. Science, 282(5388), pp. 480-483.

Rappuoli, R. & Aderem, A., 2011. A 2020 vision for vaccines against HIV, tuberculosis and malaria. Nature, 473(7348), pp. 463-469.

Reddy, S. T. et al., 2007. Exploiting lymphatic transport and complement activation in nanoparticle vaccines. Nature Biotechnology, 25(10), pp. 1159-1164.

Rejinold N S, et al., "Development of novel fibrinogen nanoparticles by two-step co-acervation method," *Int. J. Biol. Macromol.*, 47:37-43 (2010).

Riehemann, K, et al., "Nanomedicine—challenge and perspectives," *Angew. Chem. Int. Ed. Engl.*, 48:872-897 (2009).

Sakamoto, J, et al., "Antibiological barrier nanovector technology for cancer applications," *Expert Opin . . . Drug Deliv.*, 4:359-369 (2007).

Sakamoto, J H, et al., "Enabling individualized therapy through nanotechnology," *Pharmacol. Res.*, 62(2):57-89 (2010).

Sanhai, W R et al., "Seven challenges for nanomedicine," *Nat. Nanotechnol.*, 3:242-244 (2008).

Satomi, T et al., "Density control of poly(ethylene glycol) layer to regulate cellular attachment," *Langmuir*, 23:6698-6703 (2007).

Savic, R, et al., "Micellar nanocontainers distribute to defined cytoplasmic organelles," *Science*, 300:615-618 (2003).

Schijns, V. E. J. C. & Lavelle, E. C., 2011. Trends in vaccine adjuvants. Expert Review of Vaccines, 10(4), pp. 539-550.

Sengupta, S. et al., "Temporal targeting of tumour cells and neovasculature with a nanoscale delivery system, Nature, 436:568-572.

Senior, J, et al., "Influence of surface hydrophilicity of liposomes on their interaction with plasma protein and clearance from the circulation: studies with poly(ethylene glycol)-coated vesicles," *Biochim. Biophys. Acta.*, 1062:77-82 (1991).

Serda, R. E. et al. "Mitotic trafficking of silicon microparticles," *Nanoscale*, 1(2) (2009).

Serda, R E, et al., "Cellular association and assembly of a multistage delivery system," *Small*, 6:1329-1340 (2010).

Serda, R E, et al., "Mitotic partitioning of silicon microparticles," *Nanoscale*, 2:173-288 (2009).

Serda, R E, et al., "Porous silicon particles for imaging and therapy of cancer, in Nanostructured Oxides, C. S. S. R. Kumar Ed., Wiley VCH Verlag GmbH & Co. 2:357-398 (2009).

Serda, R E, et al., "Quantitative mechanics of endothelial phagocytosis of silicon microparticles," *Cytometry A*, 75:752-760 (2009).

Serda, R E, et al., "The association of silicon microparticles with endothelial cells in drug delivery to the vasculature," *Biomaterials*, 30:2440-2448 (2009).

Seubert, A et al., "Adjuvanticity of the oil-in-water emulsion MF59 is independent of Nlrp3 inflammasome but requires the adaptor protein MyD88. *Proc. Natl. Acad. Sci. USA*, 108(27):11169-11174 (2011).

Seubert, A et al., "The adjuvants aluminum hydroxide and MF59 induce monocyte and granulocyte chemoattractants and enhance monocyte differentiation toward dendritic cells," *J. Immunol.*, 180(8):5402-5412 (2008).

Sharp, F A et al., "Uptake of particulate vaccine adjuvants by dendritic cells activates the NALP3 inflammasome (2009).

Souza, G R, et al., "Combinatorial targeting and nanotechnology applications," *Biomed. Microdevices*, 12(4):597-606 (2009).

Souza, G R, et al., "Networks of gold nanoparticles and bacteriophage as biological sensors and cell-targeting agents, *Proc. Natl. Acad. Sci. USA*, 103:1215-1220 (2006).

Stohrer, M, et al., "Oncotic pressure in solid tumors is elevated," *Cancer Res.*, 60:4251-4255 (2000).

Storey, J D and Tibshirani, R. "Statistical significance for genomewide studies," *Proc. Natl. Acad. Sci. USA*, 100: 9440-9445 (2003).

Storni, T, et al., "Immunity in response to particulate antigen-delivery systems," *Adv. Drug Deliv. Rev.*, 57(3):333-5 (2005).

Tanaka, T et al., "In vivo evaluation of safety of nanoporous silicon carriers following single and multiple dose intravenous administrations in mice," *Int. J. Pharm.*, 402:190-197 (2010).

Tanaka, T, et al., "Sustained siRNA delivery by mesoporous silicon particles," *Cancer Res.*, 70:3687 (2010).

Tasciotti, E, et al., "Mesoporous silicon particles as a multistage delivery system for imaging and therapeutic applications," *Nat. Nanotechnol.*, 3:151-157 (2008).

Tasciotti, E, et al., "Porous silicon particles for multi-stage delivery," *Nanoscale Bioeng. Nanomed.*, 235-271 (2009).

Theis, T, et al., "nan'o.tech.nol'o.gy n," *Nat. Nanotechnol.*, 1:8-10 (2006).

Thiviyanathan, V, et al., "Combinatorial selection and delivery of thioaptamers," *Biochem. Soc. Trans.*, 35:50-52 (2007).

Thurston, G, et al., "Cationic liposomes target angiogenic endothelial cells in tumors and chronic inflammation in mice," *J. Clin. Invest.*, 101:1401-1413 (1998).

Tomadoni, A, et al., "Trastuzumab in the treatment of advanced breast cancer. Our single-center experience and spotlights of the latest national consensus meeting," *Medicina (B Aires)* 64:20-24 (2004).

Torchilin, V P, "Recent advances with liposomes as pharmaceutical carriers," *Nat. Rev. Drug Discov.*, 4:145-160 (2005).

Torchilin, V P, "Recent approaches to intracellular delivery of drugs and DNA and organelle targeting," *Annu. Rev. Biomed. Eng.*, 8:343-375 (2006).

Undevia, S D, et al., "Pharmacokinetic variability of anticancer agents," *Nature Rev.*, 5:447-458 (2005).

Wagner, S, et al., "Enhanced drug targeting by attachment of an anti-alpha v integrin antibody to doxorubicin loaded human serum albumin nanoparticles," *Biomaterials*, 31:2388-2398 (2010).

Wagner, V, et al., "The emerging nanomedicine landscape," *Nat. Biotechnol.*, 24:1211-1217 (2006).

Walczyk, D, et al., "What the cell "sees" in bionanoscience," *J. Am. Chem. Soc.*, 132:5761-5768 (2010).

Wan, Y Y and Flavell, R A, "How diverse—CD4 effector T cells and their functions. *J. Molec. Cell Biol*, 1(1):20-36 (2009).

Wands, J R and H E Blum, "Primary hepatocellular carcinoma," *N. Engl. J. Med.*, 325:729-731 (1991).

Wang, H.-B. & Weller, P. F., 2008. Pivotal Advance: Eosinophils mediate early alum adjuvant-elicited B cell priming and IgM production. Journal of Leukocyte Biology, 83(4), pp. 817-821.

Weitman, D S, et al., "Cellular localization of the folate receptor—potential role in drug toxicity and folate homeostasis," *Cancer Res.*, 52:6708-6711 (1992).

Wiernik, P H, et al., "Phase I clinical and pharmacokinetic study of taxol," *Cancer Res.*, (1987) 2486-2493 (1987).

Winau, F O, et al., "Paul Ehrlich—in search of the magic bullet," *Microbes Infect.*, 6:786-789 (2004).

Yoo, H S and T G Park, "Folate-receptor-targeted delivery of doxorubicin nano-aggregates stabilized by doxorubicin-PEG-folate conjugate," *J. Control Release*, 100:247-256 (2004).

Zalipsky, S, et al., "Antitumor activity of new liposomal prodrug of mitomycin C in multidrug resistant solid tumor: insights of the mechanism of action," *J. Drug Target*, 15:518-530 (2007).

Zhang, W, and Chait, B T, "ProFound: an expert system for protein identification using mass spectrometric peptide mapping information," *Anal. Chem.*, 72:2482-2489 (2000).

Zhang, X G, "Morphology and formation mechanisms of porous silicon," *J. Electrochem. Soc.*, 151:C69-C80 (2004).

Zhang, X G, et al., "Optical spectra of a novel polyoxometalate occluded within modified MCM-41," *J. Phys. Chem. B*, 109:19156-19160 (2005).

Zhu, J. and Paul, W E, "CD4 T cells: fates, functions, and faults," *Blood*, 112(5):1557-69 (2008).

Zou, Y, et al., "Lyophilized preliposomal formulation of the non-cross-resistant anthracycline annamycin: effect of surfactant on liposome formation, stability and size," *Cancer Chemother. Pharmacol.*, 39:103-108 (1996).

All of the compositions and methods disclosed and claimed herein can be made and executed without undue experimentation in light of the present disclosure. While the compositions and methods of this invention have been described in terms of exemplary embodiments, it will be apparent to those of ordinary skill in the art that variations may be applied to the composition, methods and in the steps or in the sequence of steps of the method described herein without departing from the concept, spirit and scope of the invention. More specifically, it will be apparent that certain agents that are both chemically- and physiologically related may be substituted for the agents described herein while the same or similar results would be achieved. All such similar substitutes and modifications apparent to those of ordinary skill in the art are deemed to be within the spirit, scope and concept of the invention as defined herein.

What is claimed is:

1. A composition comprising at least one first-stage porous or nanoporous silicon oxide microparticle which has (i) a body, (ii) at least one outer surface comprising toll-like receptor ligands (TLR-L); and (iii) at least one reservoir inside the body, wherein the reservoir comprises at least one second-stage nanoparticle, and wherein the reservoir further comprises antigens which are either free or encapsulated within the at least one second stage nanoparticle.

2. The composition of claim 1, wherein the body of the first-stage particle comprises a first porous region and a second porous region that differs from the first porous region in at least one property selected from the group of properties consisting of pore density, pore geometry, pore charge, pore surface chemistry and pore orientation.

3. The composition of claim 2, wherein the first porous region is configured to contain a first population of second-stage particles and the second porous region is configured to contain a second population of second-stage particles.

4. The composition of claim 1, wherein the at least one outer surface further comprises lipopolysaccharide (LPS), monophosphoryl lipid (MPL), one or more dendritic cells, one or more cytokines, or any combination thereof.

5. The composition of claim 1, wherein the at least one second-stage nanoparticle is a liposome, a nanoliposome, or a combination thereof.

6. The composition of claim 4, wherein the at least one second-stage particle further comprises a first diagnostic agent, a first therapeutic agent, a first chemotherapeutic agent, a first adjuvant, or any combination thereof.

7. The composition of claim 1, wherein the at least one first-stage particle further comprises at least one cellular-targeting moiety.

8. The composition of claim 7, wherein the at least one cellular-targeting moiety is selected from the group consisting of a chemical targeting moiety, a physical targeting moiety, a ligand moiety, a ligand targeting moiety, a geometrical targeting moiety, and any combination thereof.

9. The composition of claim 8, wherein the at least one cellular-targeting moiety comprises a plurality of distinct antigens to elicit one or more target-specific immune responses.

10. The composition of claim 8, wherein the at least one cellular-targeting moiety comprises a chemical targeting moiety disposed on the surface of the first-stage particle, wherein the chemical targeting moiety comprises at least one moiety selected from the group consisting of a ligand, a dendrimer, an oligomer, an aptamer, a binding protein, an antibody, an antigen binding fragment thereof, a biomolecule, and any combination thereof.

11. The composition of claim 1, wherein the at least one reservoir contains a plurality of tumor antigens, either free, or contained within the at least one second-stage nanoparticle.

12. The composition of claim 11, wherein the at least one reservoir further contains one or more immune-stimulating agents, one or more tumor growth inhibitors, one or more proteins, peptides, small molecules, RNA, DNA, siRNA, or any combination thereof, either free, bound to, or contained within a population of second-stage nanoparticles.

13. The composition of claim 1, wherein the first-stage particle is configured to release the at least one second-stage particle in response to an external stimulus, or to a change in the environment of the first-stage particle.

14. The composition of claim 1, wherein the at least one second stage particle is selected from the group consisting of a liposome, a micelle, an ethosome, a nanosome, a nanoliposomes, a carbon nanotube, a fullerene nanoparticle, a metal nanoparticle, a semiconductor nanoparticle, a polymer nanoparticle, an oxide nanoparticle, a viral particle, a polyionic particle and a ceramic particle.

15. The composition of claim 1, wherein the at least one second-stage particle contains at least one third-stage particle that comprises an active agent.

16. The composition of claim 6, wherein the at least one second-stage particle further comprises an imaging agent, a radiolabel, or a combination thereof.

17. The composition of claim 1, wherein the second-stage particle is selected from the group consisting of a virus, chitosan, one or more liposomes, one or more micelles, one or more PEI nanoparticles, and combinations thereof.

18. A therapeutic kit comprising the composition of claim 1, and instructions for using the composition in the diagnosis or the treatment of a mammalian cancer, or a combination thereof.

19. A method for providing an antigen to a mammalian dendritic cell comprising administering to a subject, an effective amount of the composition of claim 1.

20. The method of claim 19, wherein the subject is at risk for, is diagnosed with, or is suspected of having cancer.

21. The therapeutic kit of claim 18, wherein the mammalian cancer is human breast cancer.

22. The therapeutic kit of claim 18, wherein the composition further comprises a second therapeutic agent, a first diagnostic agent, a first imaging agent, or a combination thereof.

23. A method of administering an active agent to one or more cells, tissues, organs, or systems of a mammalian subject in need thereof, comprising administering to a mammalian subject the composition of claim 1.

24. The therapeutic kit of claim 18, wherein the composition comprises a first-stage particle that is configured for uptake by one or more antigen-presenting cells.

25. The therapeutic kit of claim 24, wherein the antigen-presenting cells comprise one or more dendritic cells.

26. The therapeutic kit of claim 18, wherein the second-stage particles comprise a population of liposomes that contain a therapeutic compound or an anti-cancer agent, or a combination thereof.

27. The method of claim 23, wherein the first-stage particle is configured to bypass a biological barrier selected from the group consisting of a hemo-rheology barrier, a reticuloendothelial system barrier, an endothelial barrier, a blood brain barrier, a tumor-associated osmotic interstitial pressure barrier, an ionic and molecular pump barrier, a cell membrane barrier, an enzymatic degradation barrier, a nuclear membrane barrier, and combinations thereof.

28. The method of claim 23, wherein the second-stage particle is selected from the group consisting of a liposome, a micelle, an ethosome, a carbon nanotube, a fullerene nanoparticle, a metal nanoparticle, a semiconductor nanoparticle, a polymer nanoparticle, an oxide nanoparticle, a viral particle, a polyionic particle, a ceramic particle, and any combination thereof.

29. The method of claim 23, wherein the body of the first stage particle comprises a first active agent and the second stage particle contains a second active agent, that is different than the first active agent.

30. The therapeutic kit of claim 18, wherein the composition is formulated for administration to the subject either orally, intranasally, intravenously, subcutaneously, or by direct injection to one or more cells or one or more tissues within or about the body of the subject.

31. The therapeutic kit of claim 18, wherein the composition is configured for contacting a population of cells obtained from a mammalian subject ex vivo, and wherein the resulting contacted cells are suitable for reintroduction into the body of the subject.

32. The method of claim 31, wherein the population of cells comprise dendritic cells.

33. The composition of claim 1, formulated as a cancer vaccine suitable for administration to a human.

34. The composition of claim 33, wherein the human has been diagnosed with breast cancer.

35. The composition of claim 1, comprised within a population of human antigen presenting cells.

36. A population of human dendritic cells comprising the composition of claim 1.

* * * * *

UNITED STATES PATENT AND TRADEMARK OFFICE
CERTIFICATE OF CORRECTION

PATENT NO. : 8,926,994 B2
APPLICATION NO. : 13/708888
DATED : January 6, 2015
INVENTOR(S) : Rita Elena Serda et al.

It is certified that error appears in the above-identified patent and that said Letters Patent is hereby corrected as shown below:

On the Title Page, Item (72) Under "Inventors"
delete "Rita Elena Serda; Ismail Mustafa Meraz; Jianhua Gu; Xiaojun Xia; Haifa Shen; Tong Sun; Mauro Ferrari"
and insert --Rita Elena Serda, Haifa Shen, Tong Sun and Mauro Ferrari--

Signed and Sealed this
Fourteenth Day of April, 2015

Michelle K. Lee
*Director of the United States Patent and Trademark Office*